(12) United States Patent
Walt et al.

(10) Patent No.: US 6,377,721 B1
(45) Date of Patent: Apr. 23, 2002

(54) BIOSENSOR ARRAY COMPRISING CELL POPULATIONS CONFINED TO MICROCAVITIES

(75) Inventors: David R. Walt, Lexington; Laura C. Taylor, Medford, both of MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 09/260,963

(22) Filed: Mar. 2, 1999

(51) Int. Cl.[7] ............................. G02B 6/00; G01N 21/00
(52) U.S. Cl. .......................... 385/12; 385/14; 385/115; 385/116; 385/117; 385/120; 385/147; 385/901; 433/808; 436/164; 436/172; 436/800; 436/805
(58) Field of Search ............................. 385/12, 13, 31, 385/33, 38, 147, 901, 14, 115, 117, 116, 120; 435/808; 359/900; 250/556; 436/164, 172, 800, 805

(56) References Cited

U.S. PATENT DOCUMENTS

| | | | |
|---|---|---|---|
| 4,200,110 A | 4/1980 | Peterson et al. | 128/634 |
| 4,499,052 A | 2/1985 | Fulwyler | 422/52 |
| 4,682,895 A | 7/1987 | Costello | 356/402 |
| 4,729,949 A | 3/1988 | Weinreb et al. | 435/30 |
| 4,772,540 A | 9/1988 | Deutsch et al. | 430/320 |

(List continued on next page.)

FOREIGN PATENT DOCUMENTS

| | | | |
|---|---|---|---|
| EP | 0 269 764 | 6/1988 | 436/528 X |
| EP | 0 392 546 | 10/1990 | 435/6 |
| EP | 0 478 319 | 4/1992 | 436/528 X |
| EP | 0 539 888 | 5/1993 | 385/12 X |
| EP | 0 723 146 | 7/1996 | 385/12 X |

(List continued on next page.)

OTHER PUBLICATIONS

Drmanac, R. et al., "Sequencing by Oligonucleotide Hybridization: A Promising Framework in Decoding of the Genome Program," The First International Conference on Electrophoresis, Supercomputing and the Human Genome, Proceeding os th Apr. 10–13, 1990 Conference at Florida State University. Ed. C. Cantor and H. Lim.

Drmanac, R. et al., "Prospects for a Miniaturized, Simplified and Frugal Human Genome Project," Scientia Yugoslavica, 16(1–2):97–107 (1990).

Drmanac, R. et al., "Sequencing by Hybridization (SBH) with Oligonucleotide Probes as an Integral Approach for the Analysis of Complex Genomes," International Journal of Genome Research, 1(1):59–79 (1992).

Drmanac, R. et al., "Sequencing by Hybridization," Automated DNA Sequencing and Analysis, ed. M. Adams, C. Fields and J. Venter. (1994).

(List continued on next page.)

*Primary Examiner*—Brian Healy
(74) *Attorney, Agent, or Firm*—Flehr Hohbach Test Albritton & Herbert LLP; Robin M. Silva; David C. Foster

(57) ABSTRACT

A biosensor, sensor array, sensing method and sensing apparatus are provided in which individual cells or randomly mixed populations of cells, having unique response characteristics to chemical and biological materials, are deployed in a plurality of discrete sites on a substrate. In a preferred embodiment, the discrete sites comprise microwells formed at the distal end of individual fibers within a fiber optic array. The biosensor array utilizes an optically interrogatable encoding scheme for determining the identity and location of each cell type in the array and provides for simultaneous measurements of large numbers of individual cell responses to target analytes. The sensing method utilizes the unique ability of cell populations to respond to biologically significant compounds in a characteristic and detectable manner. The biosensor array and measurement method may be employed in the study of biologically active materials, in situ environmental monitoring, monitoring of a variety of bioprocesses, and for high throughput screening of large combinatorial chemical libraries.

30 Claims, 9 Drawing Sheets

U.S. PATENT DOCUMENTS

| | | | |
|---|---|---|---|
| 4,785,814 A | 11/1988 | Kane | 128/634 |
| 4,822,746 A | 4/1989 | Walt | 436/528 |
| 4,824,789 A | 4/1989 | Yafuso et al. | 436/68 |
| 4,894,343 A | 1/1990 | Tanaka et al. | 385/12 X |
| 4,895,805 A | 1/1990 | Sato et al. | 385/12 X |
| 4,999,306 A | 3/1991 | Yafuso et al. | 436/68 |
| 5,002,867 A | 3/1991 | Macevicz | 435/6 |
| 5,028,545 A | 7/1991 | Soini | 436/501 |
| 5,105,305 A | 4/1992 | Betzig et al. | 339/368 |
| 5,114,864 A | 5/1992 | Walt | 436/528 |
| 5,132,242 A | 7/1992 | Cheung | 436/501 |
| 5,143,853 A | 9/1992 | Walt | 436/501 |
| 5,177,012 A | 1/1993 | Kim et al. | 435/175 |
| 5,177,013 A | 1/1993 | Kim et al. | 435/175 |
| 5,194,300 A | 3/1993 | Cheung | 427/213.31 |
| 5,244,636 A | 9/1993 | Walt et al. | 422/82.07 |
| 5,244,813 A | 9/1993 | Walt et al. | 436/172 |
| 5,250,264 A | 10/1993 | Walt et al. | 422/82.07 |
| 5,252,494 A | 10/1993 | Walt | 436/528 |
| 5,254,477 A | 10/1993 | Walt | 436/172 |
| 5,272,081 A | 12/1993 | Weinreb et al. | 435/240.1 |
| 5,298,741 A | 3/1994 | Walt et al. | 250/227.23 |
| 5,302,509 A | 4/1994 | Cheeseman | 435/6 |
| 5,310,674 A | 5/1994 | Weinreb et al. | 435/293 |
| 5,320,814 A | 6/1994 | Walt et al. | 422/82.07 |
| 5,357,590 A | 10/1994 | Auracher | 385/33 |
| 5,380,489 A | 1/1995 | Sutton et al. | 422/68.1 |
| 5,435,724 A | 7/1995 | Goodman et al. | 433/215 |
| 5,481,629 A | 1/1996 | Tabuchi | 385/14 |
| 5,494,798 A | 2/1996 | Gerdt et al. | 435/6 |
| 5,496,997 A | 3/1996 | Pope | 250/227.21 |
| 5,506,141 A | 4/1996 | Weinreb et al. | 435/309.1 |
| 5,512,490 A | 4/1996 | Walt et al. | 436/171 |
| 5,516,635 A | 5/1996 | Ekins et al. | 435/6 |
| 5,518,883 A | 5/1996 | Soini | 435/6 |
| 5,565,324 A | 10/1996 | Still et al. | 435/6 |
| 5,573,909 A | 11/1996 | Singer et al. | 435/6 |
| 5,575,849 A | 11/1996 | Honda et al. | 118/44 |
| 5,631,170 A * | 5/1997 | Attridge | 385/12 X |
| 5,633,972 A | 5/1997 | Walt et al. | 385/116 |
| 5,639,603 A | 6/1997 | Dower et al. | 435/6 |
| 5,656,241 A | 8/1997 | Seifert et al. | 422/82.07 |
| 5,671,303 A * | 9/1997 | Shieh et al. | 385/12 |
| 5,677,196 A * | 10/1997 | Herron et al. | 385/12 X |
| 5,690,894 A | 11/1997 | Pinkel et al. | 422/68.1 |
| 5,702,915 A | 12/1997 | Miyamoto | 435/32 |
| 5,846,842 A * | 12/1998 | Herron et al. | 385/12 X |
| 5,863,708 A | 1/1999 | Zanzucchi et al. | 430/320 |
| 5,888,723 A | 3/1999 | Sutton et al. | 435/5 |
| 5,900,481 A | 5/1999 | Lough et al. | 536/55.3 |
| 6,023,540 A * | 2/2000 | Walt et al. | 385/12 X |
| 6,087,114 A * | 7/2000 | Rider | 385/12 X |

FOREIGN PATENT DOCUMENTS

| | | | |
|---|---|---|---|
| FR | 2 741 357 | 5/1997 | 385/12 X |
| WO | 89/11101 | 11/1989 | 436/528 X |
| WO | 93/02360 | 2/1993 | 385/12 X |
| WO | 97/14028 | 4/1997 | 385/12 X |
| WO | 97/14928 | 4/1997 | 385/147 X |
| WO | 97/40385 | 10/1997 | 385/12 X |
| WO | 98/40726 | 9/1998 | 436/528 X |
| WO | 98/53093 | 11/1998 | 436/528 X |
| WO | 98/53300 | 11/1998 | 436/528 X |
| WO | 99/18434 | 4/1999 | 385/12 X |
| WO | 99/67414 | 12/1999 | 385/12 X |
| WO | 00/04372 | 1/2000 | 436/528 X |

OTHER PUBLICATIONS

Healey et al., "Improved Fiber–Optic chemical sensor for Penicillin,"Anal. Chem. 67(24):4471–4476 (1995).

Healey et al., "Development of a Penicillin Biosensor Using a Single zoptical Imaging Fiber,"SPIE Proc. 2388:568–573 (1995).

Abel et al., "Fiber–Optic Evanescent Wave Biosensor for the Detection of Oligonucleotides," Anal. Chem, 68:2905–2912 (1996).

Anonymous, "Microsphere Selection Guide," Bandg Laboratories, (Fisher, In) Sep. 1998.

Anonymous, "Flourescent Microspheres," Tech Note 19, Bang Laboratories (Fishers, In) Feb. 1997.

Bangs, L.B., "Immunological Applications of Microspheres," The Latex Course, Bangs Laboratories (Carmel, IN) Apr. 1996.

Barnard et al., "A Fibre–Optic Chemical Sensor with Discrete Sensing Sites," Nature, 353:338–340 (September 1991).

Ferguson et al., "A Fiber–Optic DNA Biosensor Microarray for the Analysis of Gene Expression," Nature Biotechnology, 14:1681–1684 (1996).

Fuh et al. "Single Fibre Optic Fluorescence pH Probe," Analyst 112:1159–1163 (1987).

Healey et al., "Fiberoptic DNA Sensor Array Capable of Detecting Point Mutations," Analytical Biochemistry, 251:270–279 (1997).

Hirschfield et al., "Laser–Fiber–Optic "Optrode" for Real Time In Vivo Blood Carbon Dioxide Level Monitoring," Journal of Lightwave Technology, LT–5(7):1027–1033 (1987).

Michael et al., "Making Sensors out of Disarray: Optical Sensor Microarrays," Proc. SPIE, 3270: 34–41 (1998).

Michael et al., "Fabrication of Micro–and Nanostructures Using Optical Imaging Fibers and there Use as Chemical Sensors," Proc. 3rd Intl. Symp., Microstructures and Microfabricated Systems, ed. P.J. Hesketh, et al., v.97–5, Electrochem, Soc., 152–157 (Aug.1997).

Mignani,et al., "In–Vivo Biomedical Monitoring by Fiber–Optic Systems," Journal of Lightwave Technology, 13(7): 1396–1406 (1995).

Pantano et al., "Ordered Nanowell Arrays," Chem. Mater., 8(12): 2832–2835 (1996).

Peterson et al., "Fiber–Optic Sensors for Biomedical Applications," Science, 13:123–127 (1984).

Peterson, J. et al., "Fiber Optic pH Probe for Physiological Use," Anal. Chem., 52:864–869 (1980).

Piunno et al.,"Fiber–Optic DNA Sensor for Fluorometric Nucleic Acid Determination," Anal. Chem., 67:2635–2643 (1995).

Pope, E. "Fiber Optic Chemical Microsensors Employing Optically Active Silica Microspehres," SPIE, 2388:245–256 (1995).

Strachan et al., "A Rapid General Methaod for the Identification of PCR Products Using a Fibre–Optic Biosensor and its Application to the Detection of Listeria," Letters in Applied Microbiology,21:5–9 (1995).

Walt, "Fiber–Optic Sensors for Continuous Clinical Monitoring," Proc.IEEE, 80(6): 903–911 (1992).

Deutsch, et al., "Apparatus for high Precision Repetitive Sequential Optical Measurement of Living Dells," *Cytometry* 16:214–226 (1994).

Zurgil, et al., "Intracellular Fluorescence Polanization Measurements by the Cellscan System: Detection of Cellular Activity in Autoimmune Disorders," *Isr. J. Med. Sci.* 33:273–279 (1997).

Deutsch, et al., "Lymphocyte Fluorescence Polarization Measurements with the Cellscan System: Application to the SCM Cancer Test," *Cytometry* 23:159–165 (1996).

Rahmani, et al., "Adaption of the Cellscan Technique for the SCM Test in Breast Cancer," European *J. Cancer* 32A(10): 1758–1765 (1996).

Birindelli, et al., "Comments on Adaptation of the Cellscan Technique for the SCM Test in Breast Cancer," *European J. Cancer* 33(8):1333–1334 (1997).

Normie, L. "System Uses Photonics for Early Tumor Detection," *Biophotonics International* 24–25 (September/October 1996).

Mrksich,et al., "Controlling Cell Attachment of Contored Surfaces with Self–assemble Monolayers of Alkanethiolates on Gold," *Proc. Natl. Acad. Sci.* USA 93:10775–10778 (Oct.1996).

Park,et al., "Block Copolymer Lithography: Periodic Arrays of ~10**11 Holes in 1 square Centimeter," *Science* 276:1401–1404 (May 1997).

Clark, et al.,"Electrochemical Analysis in Picoliter Microvials,"*Anal. Chem.* 69:259–263 (1997).

Owicki, et al., "The Light Addressable Potentiometric Sensor: Principles and Biological Applications,"*Annu. Rev. Biophys, Biomol. Struct.* 23:87–113 (1994).

Hafeman, et al., "Light–Addressable Potentiometric Sensor for Biochemical Systems,"*Science* 240:1182–1184 (May 1988).

Parce, et al., "Biosensors for Directly Measuring Cell Affecting Agents,"*Ann. Biol. Clin.* 48:639–641 (1990).

McConnell, et al., "The Cytocensor Microphysiometer: Biological Applications of Silicon Technology,"*Science* 257:1906–1912 (Sep. 1992).

Owicki, et al., "Bioassays with a Microphysiometer,"*Nature* 344:271–272 (Mar. 1990).

Parce, et al., "Detection of Cell–Affecting Agents with a Silicon Biosensor,"*Science* 246:243–247 (Oct.1989).

Hogan, et al., "Single–cell Analysis at the level of a Single Human Erythrocyte," Trends in Analytical *Chemistry* 12(1):4–9 (1993).

Yeung, E.S. "Chemical Analysis of Single human Erythrocytes,"*Acc. Chem. Res.* 27:409–414 91994).

Shear, et al., "Single Cells as Biosensors for Chemical Separations,"*Science* 267:74–77v(1995).

Gauci, et al., "Observation of Single–Cell Fluorescence Spectra in Laser Flow Cytometry," *Cytometry* 25:388–393 (1996).

Huang, et al., "Exploring Single–cell Dynamics Using Chemically–modified Microelectrodes," *Trends in Analytical Chemistry* 14(4):158–164 (1995).

Zare, R.N. "Making a Biosensor from a Cell and a Fluorescent Dye," *Biophotonics International*,17 (Mar./Apr. 1995).

Castano, et al., "Dynamic Monitoring and Quantification of Gene Expression in Single Living Cells:a Molecular Basis for Secretory Cell heterogeneity," *Mol. Endo.* 10(5):599–605 (1996).

Owicki, et al., "Continuous Monitoring of Receptor–Mediated Changes in the Metabolic Rates of Living Cells," *Proc. Natl. Acad. Sci.* USA 87:407–4011 (1990).

Wightam, et al., "Monitoring Catechollamines at Single Cells," *Trends in Analytical Chemistry* 14(4): 154–158 (1995).

Chiavaroli, et al., "Simultaneous Monitoring of Cytosolic Free Calcium and Exocytosis at the Single Cell Leve," *J. Neuroendocrinology* 3(3):253–260 (1991).

Koop, et al., "Continuous Monitoring of Cytoplasmic ATP in Single Isolated Rat Hepatocytes During Metaboli Poisoning," *Biochem. J.* 295:165–170 (1993).

Tong, et al, "Monitoring Single Cell Pharmacokinetics by Capillary Electrophoresis and Laser–induced native Fluorescence,"*J. Chromatography B.* 689:321–325 (1997).

Wong, et al., "Simultaneous Monitoring of Glutathione and Major Proteins in Single Erthrocytes," *Mikrochim. Acta.* 120:321–327(1995).

Boltz, et al., "A Disposable–Chamber Temperature–Regulation System for the Study of Intracellular Calcium Levels in Single Live T Cells Using Fluorescence Digital–Imaging Microscopy," *Cytometry* 17:128–134 (1994).

Ince, et al., "A Micro–Perfusion Chamber for Single–Cell Fluorescence Measurements," *Journal of Immunological Methods* 128:227–234 (1990).

Luong, et al., "Fluorescence Sensors for Monitoring Bioprocesses," Practical Fluoro, ed. G.G. Guilbault, 2nd Ed., Marcel Dekker. 775–793 (New York 1990).

Hughes, et al., "New Fluorescence Tools for Investigating Enzyme Activity," *Analytica Chimica Acta* 307:393–402 (1995).

Tsien, "Fluorescent Probes of Cell Signaling," *Ann. Rev. Neurosci.* 12:227–253 (1989).

Regnier, et al., "Electrophoretically–mediated Microanalysis," Trends in Analytical Chemistry, 14(4);177–181 (1995).

Ramanathan, et al., "Sensing Antimonite and Arsenite at the Subattomole Level with Genetically Engineered Bioluminescent Bacteria," Anal. Chem. 69:3380–3384 (1997).

Niswender, et al., "Quantitative Imaging of Green Fluorescent Protein in Cultured Cells: Comparison of Microscopic Techniques, Use in Fusion Proteins and Detection Limits," *Journal of Microscopy* 180(part 2): 1096–116 (Nov. 1995).

Cubitt, et al., "Understanding, Improving and Using Green Fluorescent Proteins," *TIBS,* 20:448–455 (Nov. 1995).

Gura, "Jellyfish Protein Lights Up Cells," *Science* 276:1989 (1997).

Mlyawaki, et al., "Fluorescent Indicators for Ca2+ Based on Green Fluorescent Proteins and Calmodulin," *Nature* 388:882–887 (Aug. 1997).

Hughes, et al., "Fluorescence Imaging of Whole Microorganisms with Scientific Grade CCDS,"Special Publication Royal Society of Chemistry (Great Britain). 194:184–189 (1996).

\* cited by examiner

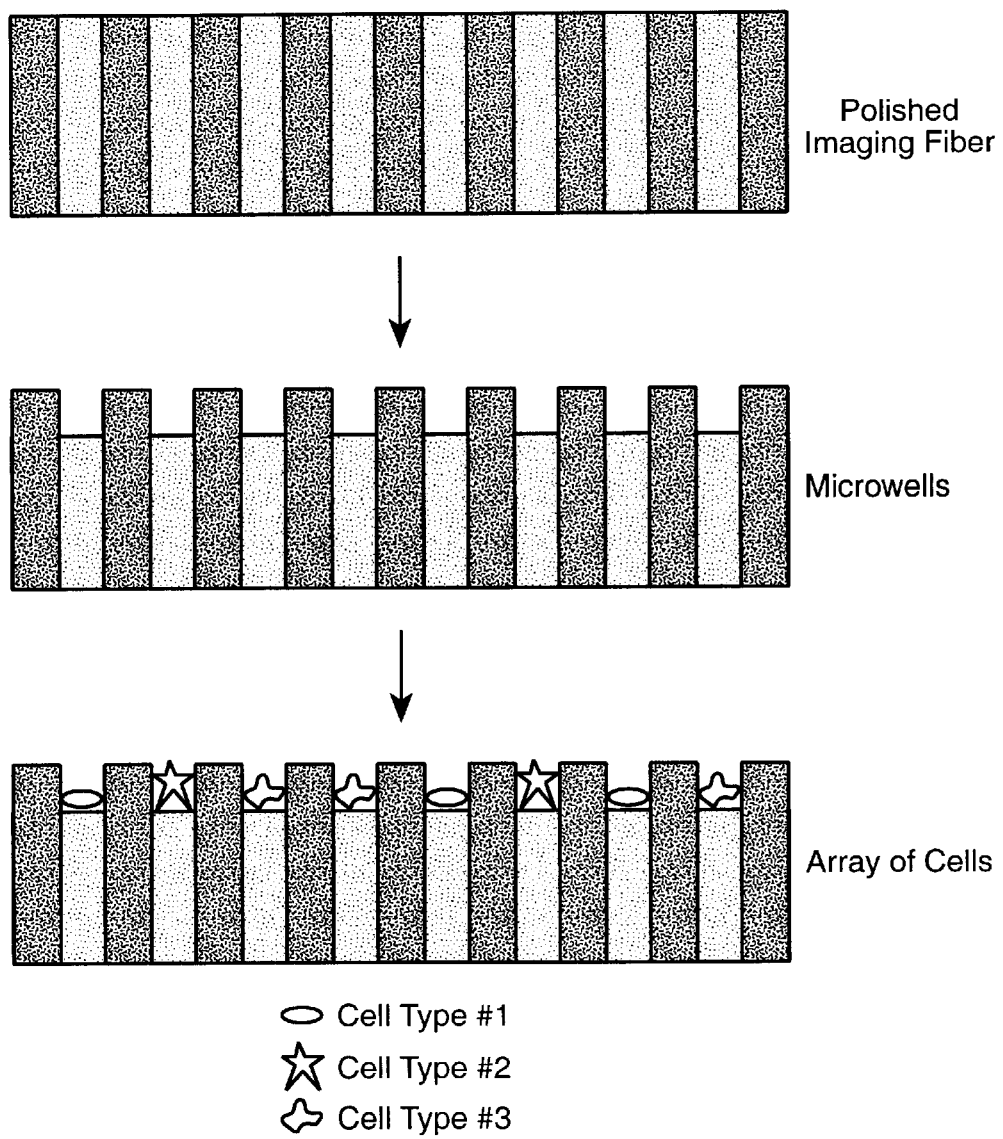
FIG._1

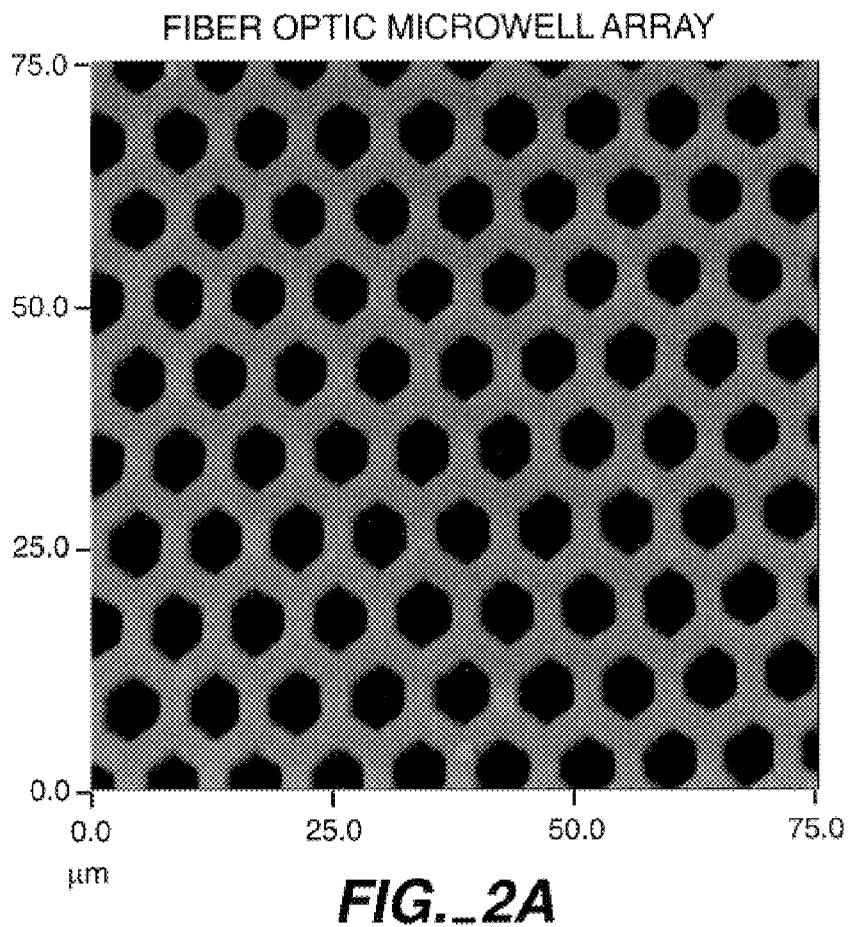
FIG._2A
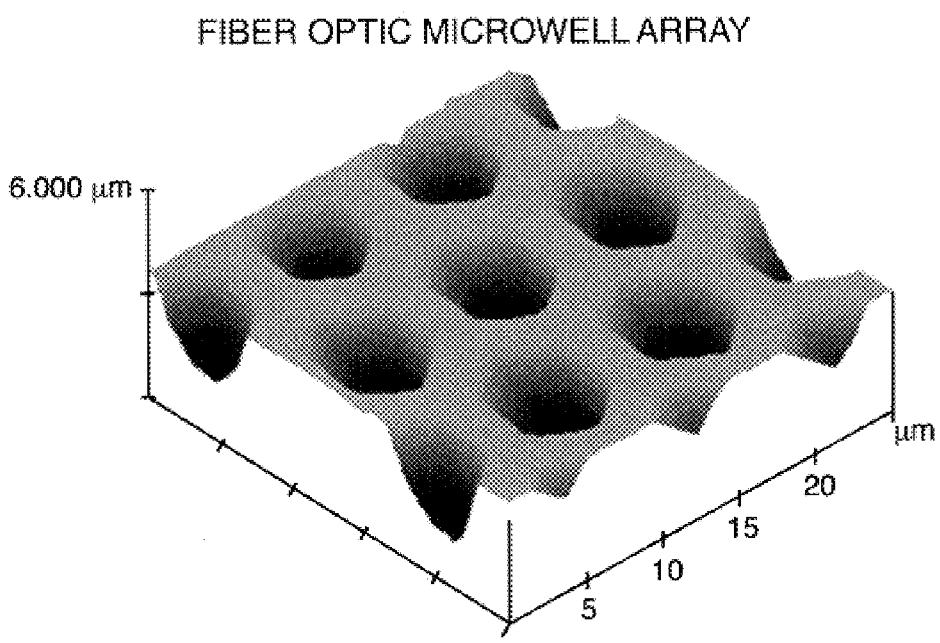
FIG._2B

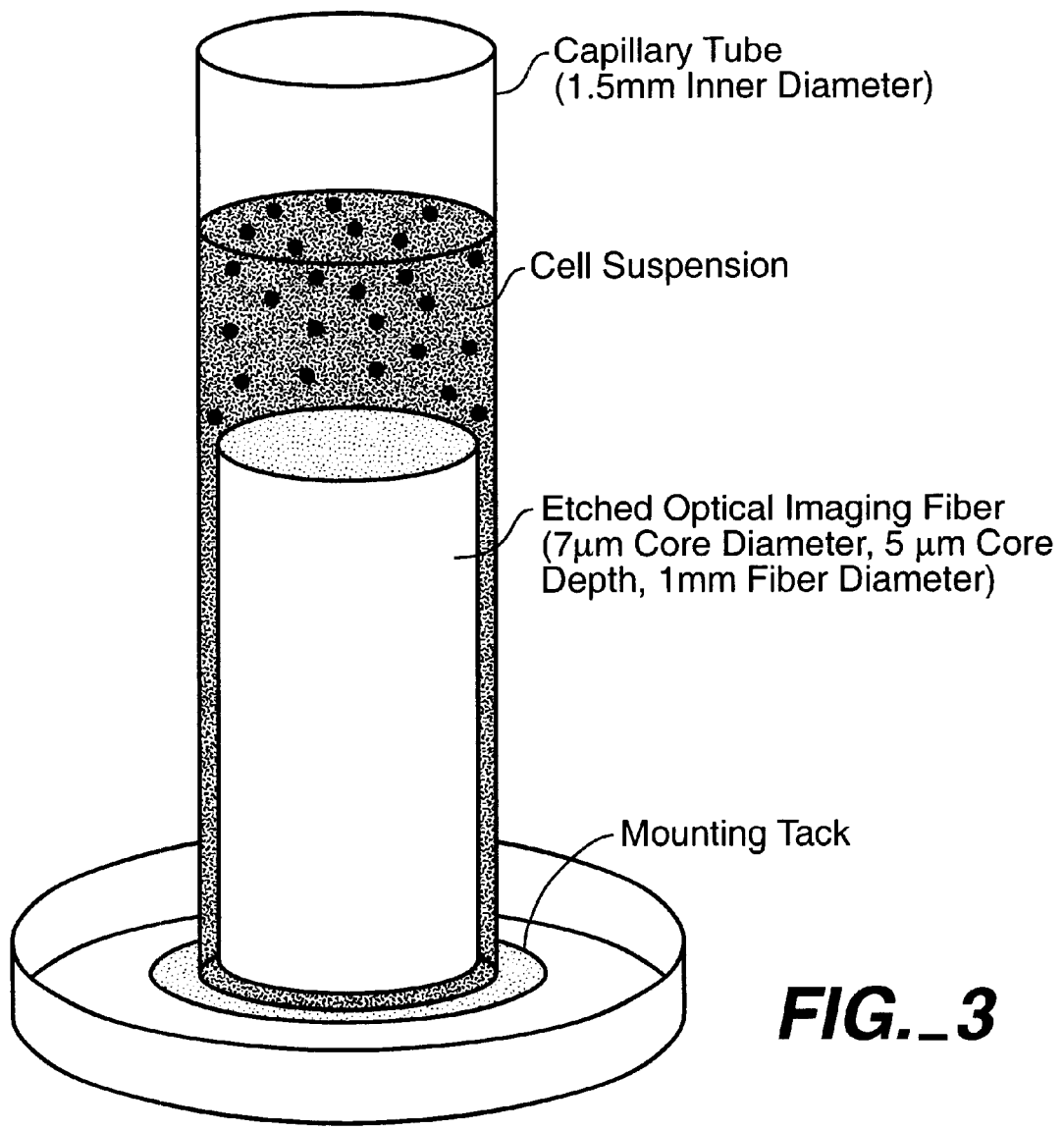
FIG._3

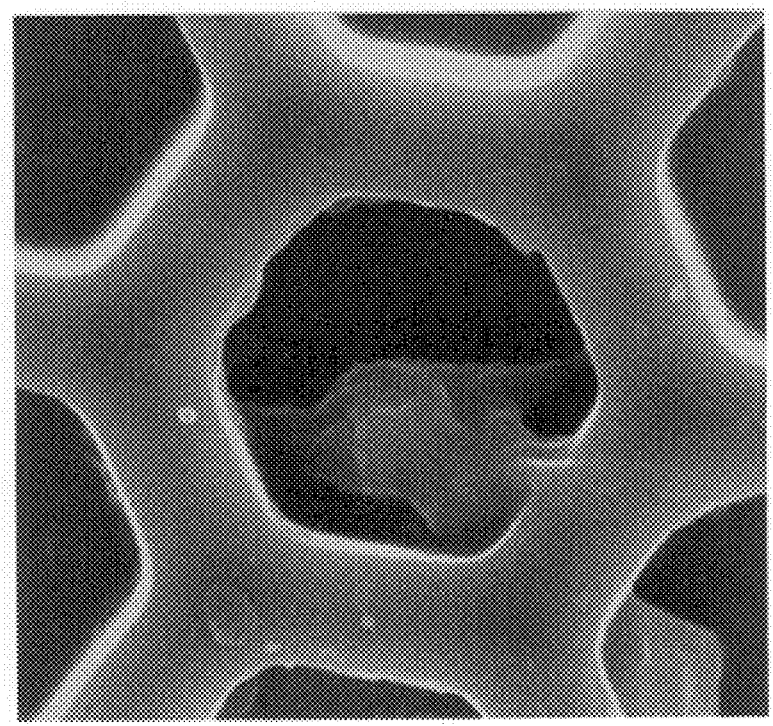
FIG._4
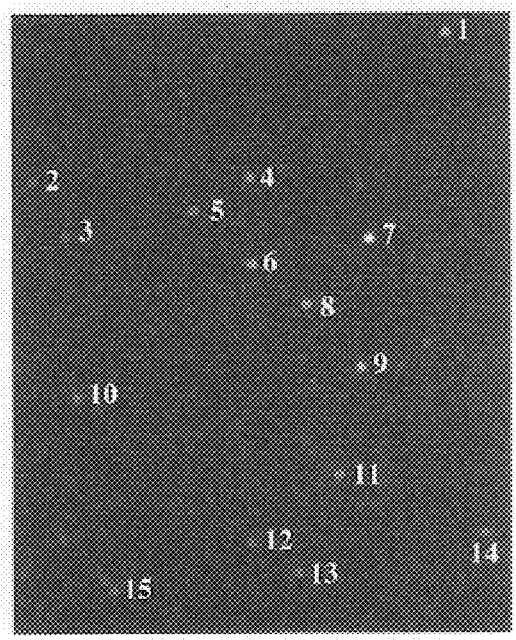
FIG._6

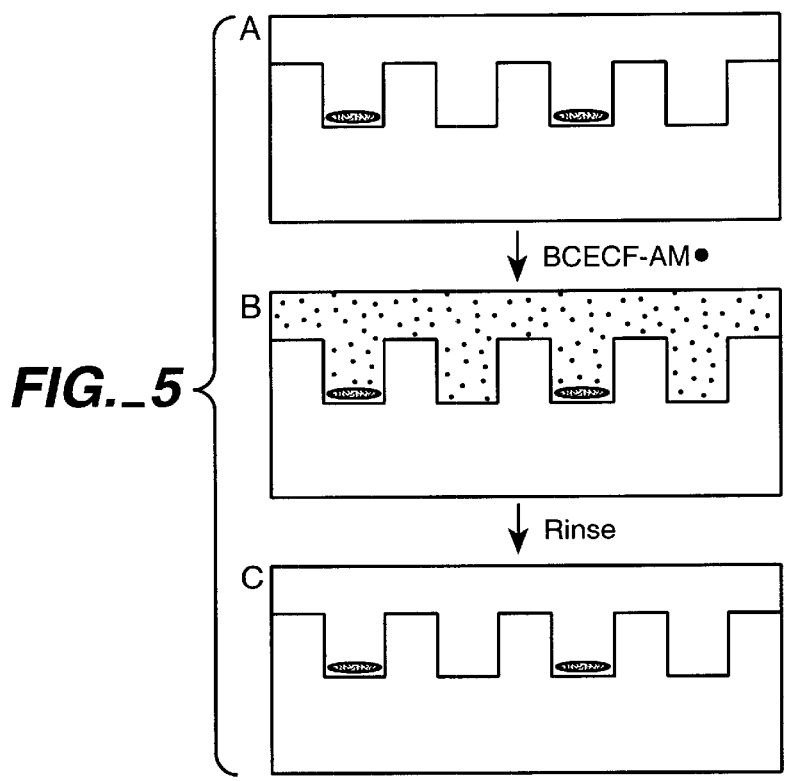
FIG._5
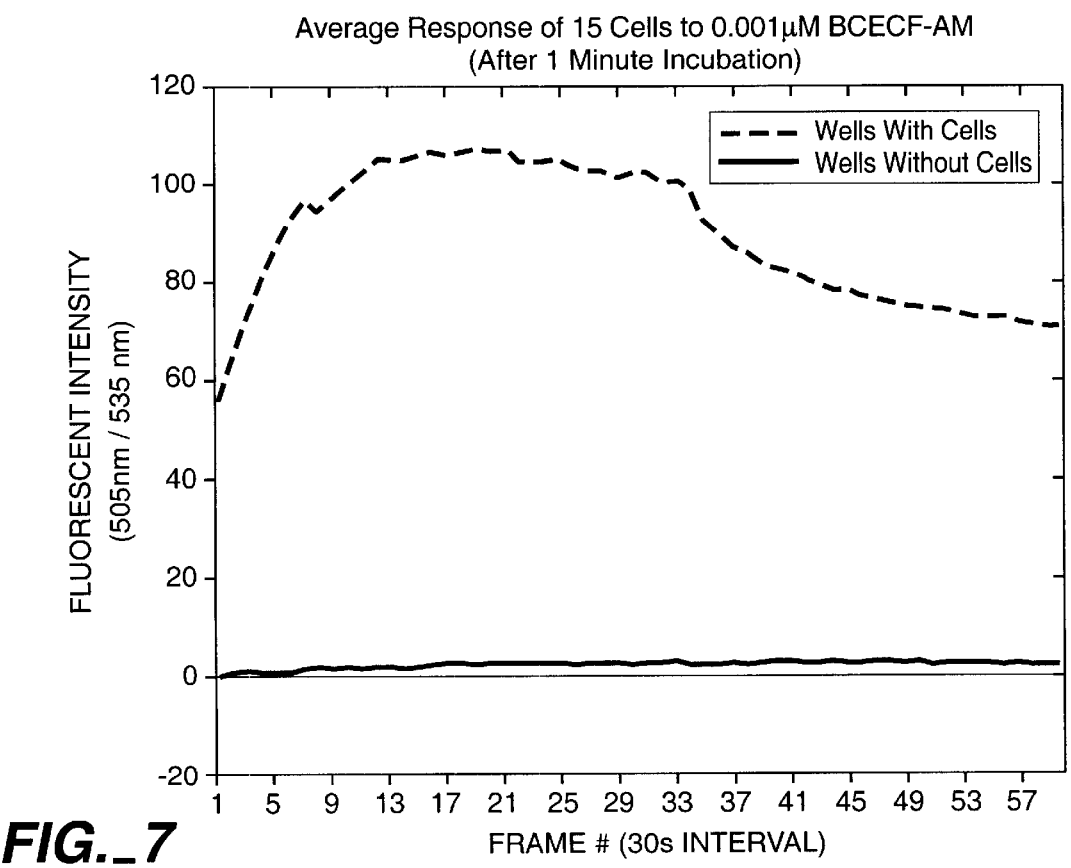
FIG._7

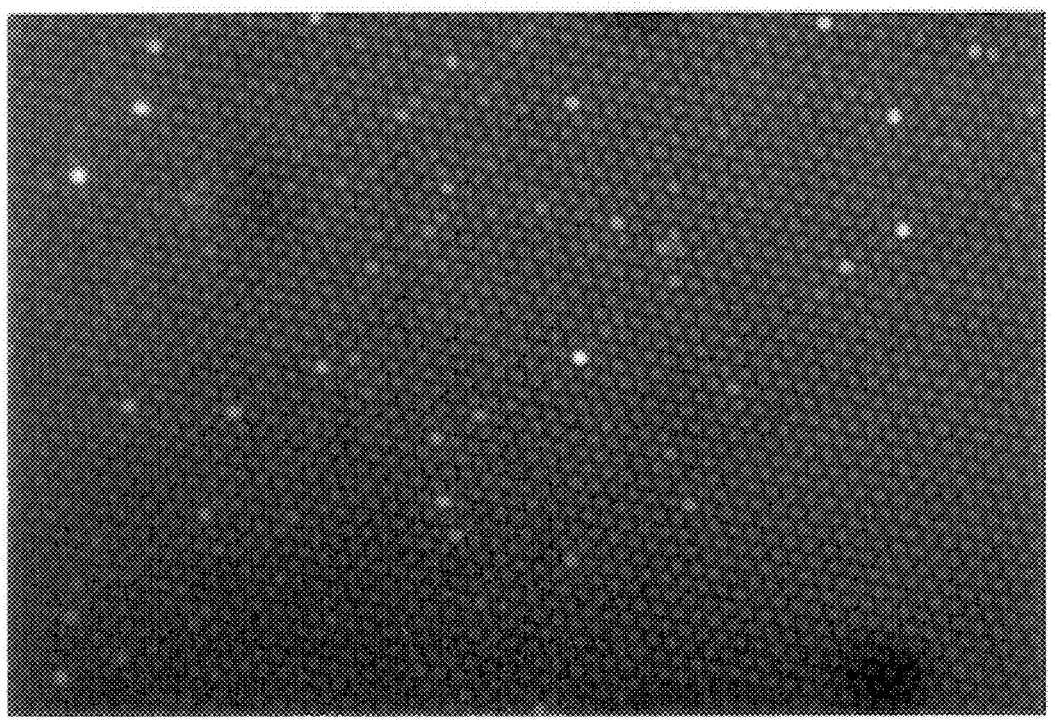
- 7µm Core Diameter
- 5µm Core Depth
- 145 fL Well Volume
FIG._8

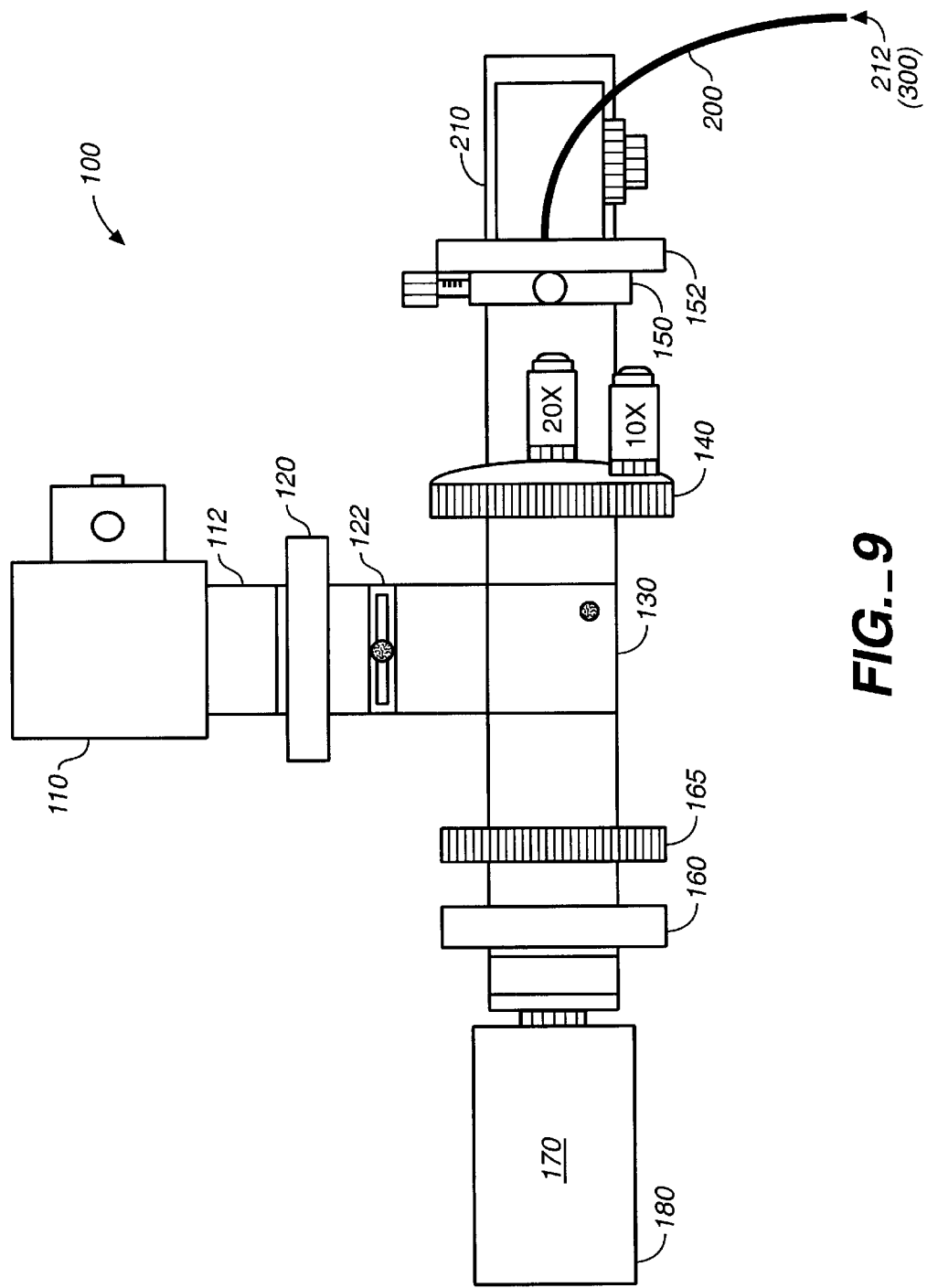
FIG._9

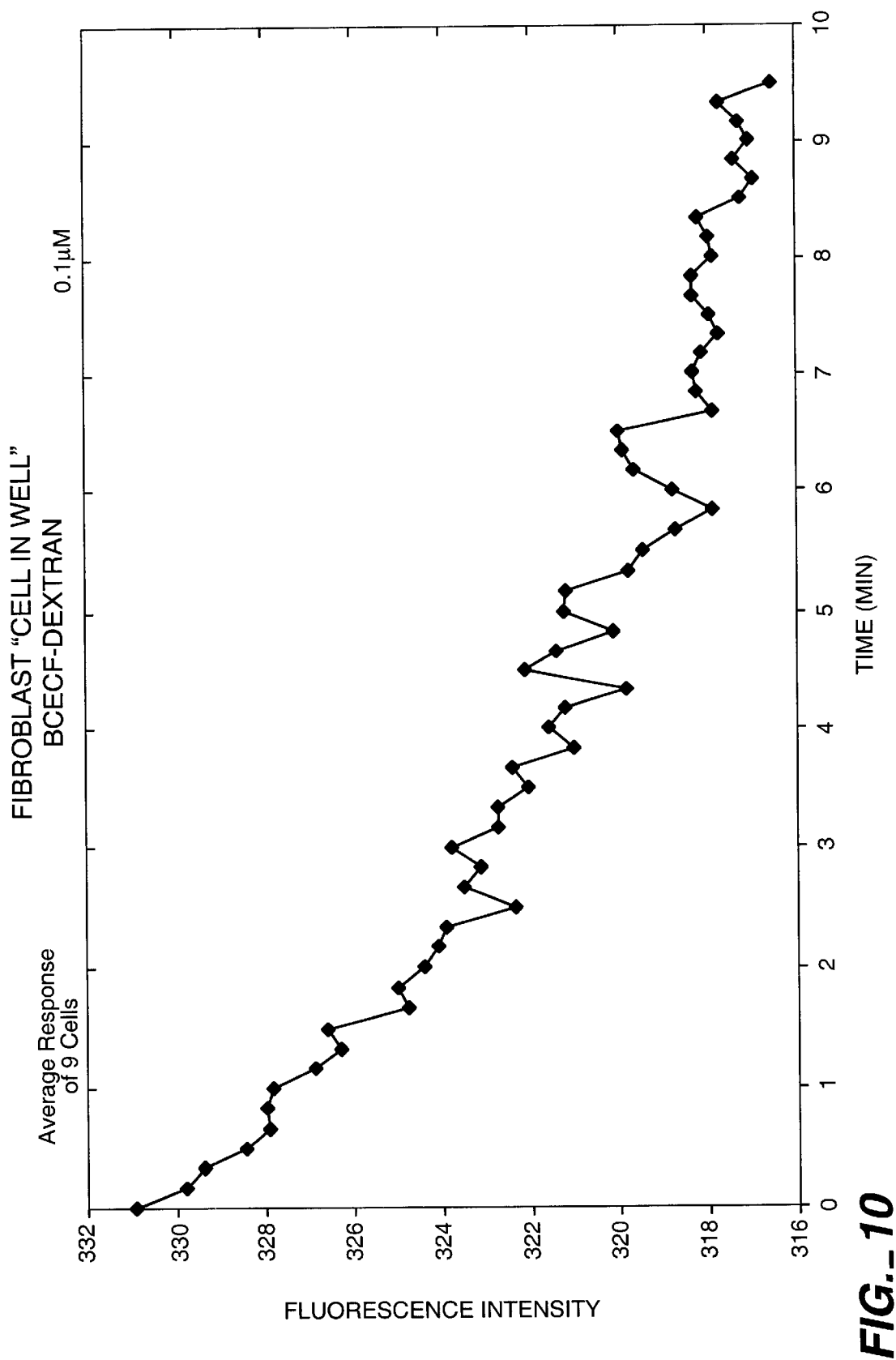
FIG._10

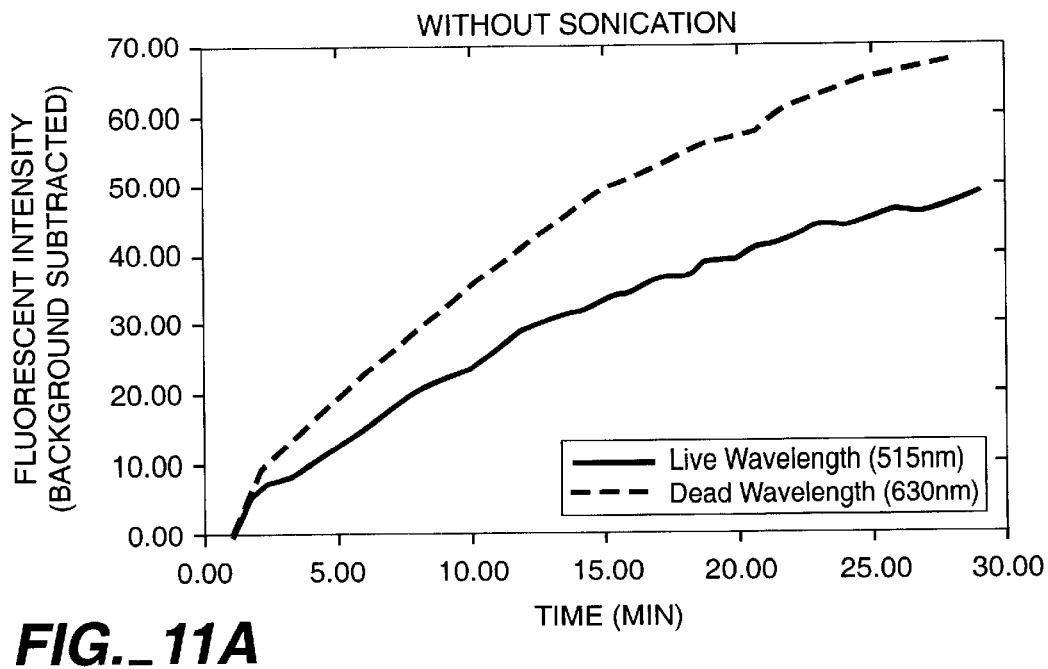
FIG._11A
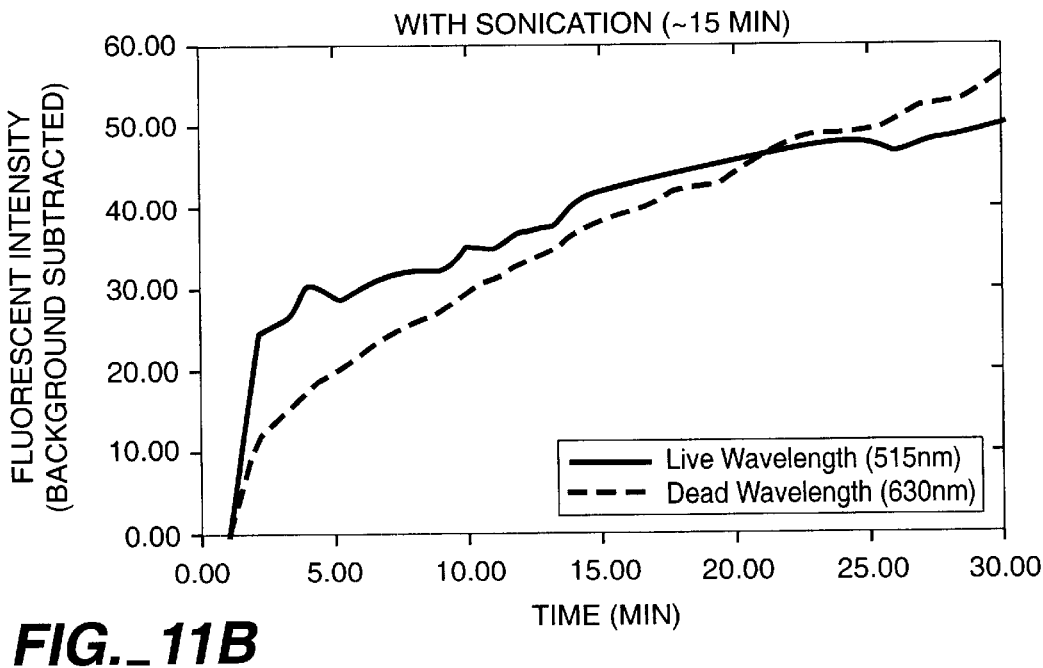
FIG._11B

BIOSENSOR ARRAY COMPRISING CELL POPULATIONS CONFINED TO MICROCAVITIES

This invention was made with government support under GM48142 awarded by the National Institutes of Health. The government has certain rights in the invention.

FIELD OF THE INVENTION

The present invention is generally concerned with biosensors, biosensor arrays, and sensing apparatus, and sensing methods for the analysis of chemical and biological materials. More particularly, the invention is directed to biosensors, biosensor arrays, sensing apparatus and sensing methods which employ cells and mixed populations of cells for analysis of chemical and biological materials.

BACKGROUND OF THE INVENTION

It is generally recognized that important technical advances in chemistry, biology and medicine benefit from the ability to perform microanalysis of samples in minute quantities. However, making analytical measurements on minute quantities has long been a challenge due to difficulties encountered with small volume sample handling, isolation of analytes, and micro-analysis of single-cell physiology.

Nanoliter, picoliter, and femtoliter volume studies have been explored in a range of applications involving in vitro and in vivo cellular investigations [R. M. Wightman, et al., *Proc. Natl. Acad. Sci. U.S.A.* 88:10754(1991); R. H. Chow, et al. *Nature* 356:60(1992); T. K. Chen, et al. *Anal. Chem.* 66:3031(1994); S. E. Zerby, et al., *Neurochem.* 66:651 (1996); P. A. Garis, et al. *J. Neurosci.* 14:6084(1994); G. Chen, et al., *J. Neurosci.* 15:7747(1995)], electrochemistry [R. A. Clark, et al., *Anal. Chem.* 69(2):259(1997)], matrix-assisted laser desorption—ionization mass spectrometry [S. Jespersen, et al., *Rapid Commun. Mass Spectrom.* 8:581 (1994)], micro-column liquid chromatography [I. A. Holland, et al., *Anal. Chem.* 67:3275(1995); M. D. Oates, et al., *Anal. Chem.* 62:1573(1990)], micro-titration [M. Gratzl. et al *Anal. Chem.* 65:2085(1993); C. Yi, et al., *Anal. Chem.* 66:1976(1994)], and capillary electrophoresis [M.Jansson, et al., *J. Chromatogr.* 626:310(1992); P. Beyer Hietpas, et al. *J.Liq.Chromatogr.* 18:3557(1995)].

Clark, et al. [*Anal. Chem.* 69(2):259(1997)] has disclosed a method for fabricating picoliter microvials for electrochemical microanalysis using conventional photolithographic masking and photoresist techniques to transfer mold polystyrene microvials on silicon wafer templates. These microvials typically exhibit non-uniformity in size and shape due to the difficulty in controlling the resist etching of the molding surface and the transfer molding process.

Park, et al. [*Science* 276:1401(1997)] has disclosed a modified lithographic method for producing arrays of nanometer-sized holes using polystyrene-polybutadiene, ordered, diblock copolymers as masks in reactive ion etching of silicon nitride. This multi-step method is capable of producing arrays of picoliter-sized holes which are typically 20 nanometers in diameter and 20 nanometers deep with a spacing of 40 nanometers. Hole densities of up to $10^{11}$ holes/cm$^2$ are disclosed. The range of sizes and spacings of the holes produced by this method is limited by the size of the copolymer microdomains. Uniformity of hole size and spacing is difficult to maintain with this method due to difficulties in controlling the etching method employed to form the holes.

Deutsch, et al. [*Cytometry* 16:214(1994)] have disclosed a porous electroplated nickel microarray comprised of micron-sized conical holes in blackened nickel plate. Hole sizes range from a 7 um upper diameter to a 3 um lower diameter with an 8 um depth. The array is used as a cell carrier for trapping individual cells while studying the responses of individual cells to changes in their microenvironment. In U.S. Pat. No. 4,772540, Deutsch, et al., have also disclosed a method for making such an array using a combined photoresist and electroplating technique.

Corning Costar Corp. (Acton, Mass.) produces a commercial microwell array for miniaturized assays under the trademark PixWell™. These arrays are made from micro-formed glass plates and comprise 40 um diameter by 20 um deep tapered wells with a well density of 4356 wells/cm$^2$.

Microwell arrays have particular utility in the study of living cells. In cell research, the measurement of responses of individual cells to changes or manipulations in their local environment is desirable. Any method or device designed for such studies must provide for the capability of maintaining cell viability, identifying the location of individual cells, and correlating response measurements with individual cells.

Due to the availability of viable fluorescent probes for intracellular studies, fluorescence measurements of living cells have significant utility in the study of cell functions. Thus fluorescence optical measurements are often utilized in cell studies where three generic methods of cell measurement are available, comprising bulk measurements of cell populations, dynamic measurements of cell populations or individual cells, and static measurements of individual cells.

The characteristics of an entire cell population as a whole can be studied with bulk measurements of sample volumes having a plurality of cells. This method is preferred where cell populations are very homogeneous. A generally recognized limitation of this method is the presence of background fluorescence which reduces the sensitivity of measurements and the inability of distinguishing differences or heterogeneity within a cell population.

Flow cytometry methods are often employed to reduce problems with background fluorescence which are encountered in bulk cell population measurements [M. R. Gauci, et al., *Cytometry* 25:388(1996); R. C. Boltz, et al., *Cytometry* 17:128(1994)]. In these methods, cell fluorescence emission is measured as cells are transported through an excitation light beam by a laminar flowing fluid. Flow cytometry methods may be combined with static methods for preliminary sorting and depositing of a small number of cells on a substrate for subsequent static cell measurements [U.S. Pat. No. 4,009,435 to Hogg, et al.; Kanz, et al., *Cytometry* 7:491(1986); Schildkraut, et al., *J. Histochem Cytochem* 27;289(1979)].

Gauci, et al., disclose a method where cell size, shape and volume is measured by light scattering and fluorescent dyes are utilized to determine protein content and total nucleic acid content of cells. This method further provides for counting and sizing various cells at a rate of approximately 100 cells per second.

Flow cytometry techniques are generally limited to short duration, single measurements of individual cells. Repetitive measurements on the same cell over time are not possible with this method since typical dwell times of a cell in the excitation light beam are typically a few microseconds. In addition, the low cumulative intensity from individual cell fluorescence emissions during such short measurement times reduces the precision and limits the reliability of such measurements.

Regnier, et al., [*Trends in Anal. Chem.* 14(4):177(1995)] discloses an invasive, electrophoretically mediated, microanalysis method for single cell analysis. The method utilizes a tapered microinjector at the injection end of a capillary electrophoresis column to pierce an individual cell membrane and withdraw a sample of cytoplasm. The method measures cell contents, one cell at a time. The method is generally limited to the detection of easily oxidized species.

Hogan, et al., [*Trends in Anal. Chem.* 12(1):4(1993)] discloses a microcolumn separation technique which may be utilized in combination with either a conventional gas chromatograph-mass spectrometer, micro thin layer chromatography or high pressure liquid manipulation of small cellular volumes. The sensitivity of the method is limited and may require pre-selection of target compounds for detection.

Static methods are generally the preferred method for measurements on individual cells. Measurement methods range from observing individual cells with a conventional optical microscope to employing laser scanning microscopes with computerized image analysis systems [see L. Hart, et al., *Anal. Quant Cytol. Histol.* 12:127(1990)]. Such methods typically require the attachment of individual cells to a substrate prior to actual measurements. Problems are typically encountered in attaching single cells or single layers of cells to substrates and in maintaining cells in a fixed location during analysis or manipulation of the cell microenvironment. Additionally, repetitive measurements on individual cells typically require physically indexing the location of individual cells and providing a mechanism for scanning each cell sequentially and returning to indexed cell locations for repeated analysis of individual cells.

Huang, et al., [*Trends in Anal. Chem.*, 14(4)158(1995)] discloses a static electrochemical method and electrode for monitoring the biochemical environment of single cells. The method requires fabrication and manual positioning of a microelectrode reference and working electrode within the cell. The method has been used to detect insulin, nitric oxide and glucose inside single cells or external to the cells. The method is generally limited to the study of redox reactions within cells.

Ince, et al. [*J. Immunol. Methods* 128:227(1990)] disclose a closed chamber device for the study of single cells under controlled environments. This method employs a microperfusion chamber which is capable of creating extreme environmental conditions for cell studies. Individual cells are held in place by two glass coverslips as various solutions are passed through the chamber. One limitation of the method is the difficulty in eliminating entrapped gas bubbles which cause a high degree of autofluorescence and thus reduces the sensitivity of measurements due to background fluorescence.

In an attempt to overcome the limitations encountered with conventional static methods, Deutsch, et al., [*Cytometry* 16:214(1994)] and Weinreb and Deutsch, in U.S. Pat. Nos. 4,729,949, 5,272,081, 5,310,674, and 5,506,141, have disclosed an apparatus and method for repetitive optical measurements of individual cells within a cell population where the location of each cell is preserved during manipulation of the cell microenvironment.

A central feature of the apparatus disclosed by Deutsch, et al., is a cell carrier, comprising a two dimensional array of apertures or traps which are conical-shaped in order to trap and hold individual cells by applying suction. The cell carrier is typically fabricated by the combined electroplating-photoresist method disclosed in U.S. Pat. No. 4,772540 to Deutsch, et al. The purpose of the cell carrier is to provide a means for maintaining the cells in fixed array locations while manipulating the cell environment. Individual cells are urged into cell carrier holes by suction and the wells are subsequently illuminated with a low-intensity beam of polarized light that reads back-emitted polarization and intensity. Measurements are compared when two different reagents are sequentially reacted with the cells. The method as disclosed requires two separate cell carriers for both a baseline control and analyte measurement.

The method and device of Deutsch, et al., have been employed by pathologists in diagnostic tests to determine the health and viability of cell samples taken from patients. The method and device have been applied to both cancer screening [Deutsch, et al., *Cytometry* 16:214(1994), *Cytometry* 23:159(1996), and *European J. Cancer* 32A(10):1758 (1996)] and rheumatoid arthritis [Zurgil, et al., *Isr.J.Med.Sci.* 33:273(1997)] in which fluorescence polarization measurements are used to differentiate lymphocytes of malignant versus healthy cells based on changes in the internal viscosity and structuredness of the cytoplasmic matrix induced by exposure to tumor antigen and mitogens.

The method and device disclosed by Deutsch, et al., requires employment of a scanning table driven by three stepping motors and a computer control system for mapping, indexing and locating individual cells in the cell carrier. The use of such mechanical scanning methods introduces limitations in reproducibility and accuracy of measurements due to conventional mechanical problems encountered with backlash and reproducible positioning of individual cell locations for repeated measurements. In addition, mechanical scanning of the entire array prolongs the measurement time for each cell in the array.

The method disclosed by Deutsch, et al., is further limited by the use of fluorescence polarization measurements which have certain intrinsic limitations due to the significant influence of various optical system components on polarization as the fluorescence emission response is passed from the cell carrier to optical detectors. Birindelli, et al. [*European J. Cancer* 33(8):1333(1997)], has also identified limitations in this method due to fluctuations in electropolarisation values which require taking averages of at least three measurement scans for each condition so as to obtain reliable measurements. In addition, for cell studies, polarization measurements are generally limited to cell responses which produce sufficient changes in cytoplasm viscosity to produce a detectable change in polarization. Since not all cell responses are accompanied by detectable viscosity changes, the method is further limited to the cell activities which create such viscosity changes in the cytoplasm.

Zare, et al., [*Science* 267:74(1995); *Biophotonics International*, March–April, p17 (1995)] discloses a biosensor system based on the response of living cells to complex biological materials fractionated by a microcolumn separation technique. Cells which were positioned on a glass cover slip were treated with a fluorescent probe and subsequently shown to be sensitive to a series of biological compounds including acetylcholine, bradykinin, and adenosine triphosphate as well as changes in intracellular calcium levels.

Yeung, et al. [*Acc. Chem. Res.* 27:409(1994)] has reviewed a number of methods for single cell response studies and has observed a significant variation and heterogeneity within cell populations based on analyte measurements. For example, the reference discloses a capillary electrophoresis method for exposing cells to biologically reactive compounds, extracting the intracellular fluid of individual cells produced in response to such compounds, and identifying analytes from migration times in the capillary column. Other fluorescence-based assays are also disclosed. Significant cell-to-cell variations and heterogeneity in individual cell responses within a cell population were observed which differences could provide a means for discriminating between biological and chemical compounds in contact with individual cells.

McConnell, et al. [*Science,* 257:1906(1992)], disclose a microphysiometer device known as the "Cytosensor" which uses a light addressable potentiometer sensor to measure the rate at which cells acidify their environment. This sensor acts as miniaturized pH electrode for monitoring cell responses which produce detectable changes in local pH. The disclosed device is limited to the measurement of proton excretions from cells and thus is only capable of detecting acidic cell responses to analytes.

U.S. Pat. No. 5,177,012 to Kim, et al., disclose a biosensor for the determination of glucose and fructose. The biosensor is produced by treating whole cells with an organic solvent and immobilizing the treated cells residue on a support to form a whole cell membrane which is applied to a pH electrode.

U.S. Pat. No. 5,690,894 to Pinkel, et al., discloses a biosensor which employs biological "binding partners", materials such as nucleic acids, antibodies, proteins, lectins and other materials derived from cells, tissues, natural or genetically-engineered organisms. These agents are used in conjunction with a fiber optic array where each species of binding partners is uniquely addressed by a group of fibers within the fiber optic bundle which is coupled to an optical detector. The array was designed for screening of extensive arrays of biological binding partners.

While many of the prior art methods provide for the analysis of either single cells or populations of cells and some of these methods provide for monitoring cell responses to target analytes, none of the disclosed methods provides for employing large populations of monocultures or mixed populations of living cells for simultaneously monitoring the responses of individual cells to biological stimuli produced by chemical and biological analytes. Thus there is a need for a biosensor array and method which efficiently utilizes the ability of populations of living cells to respond to biologically significant compounds in a unique and detectable manner. Since the selectivity of living cells for such compounds has considerable value and utility in drug screening and analysis of complex biological fluids, a biosensor which makes use of the unique characteristics of living cell populations would offer distinct advantages in high throughput screening of combinatorial libraries where hundreds of thousands of candidate pharmaceutical compounds must be evaluated. In addition, such a sensor would be useful in monitoring bioprocesses and environmental pollution where the enhanced sensitivity of living cells to their environment can be exploited.

SUMMARY OF THE INVENTION

In general, the invention provides for a biosensor, a biosensor array, a biosensor sensing system and sensing methods for the analysis of chemical and biological materials. More particularly, the invention provides for biosensors and biosensor arrays, sensing apparatus and sensing methods which employ living cells and mixed populations of living cells for analysis of chemical and biological materials.

The biosensor array of the present invention comprises either a monoculture of living cells or randomly mixed populations of living cells wherein each individual cell in the array is positioned on a substrate at an optically-addressable, discrete site which accomodates the size and shape of individual cells. In one embodiment, the discrete site comprises a microwell or microcavity which is preformed to accommodate the size and shape of the individual cells. The biosensor array sensing method relies on the well known fact that individual cells, which are chemically or biologically stimulated by the presence of a biological or chemical material in the cell environment, will respond by producing a change in the cell or cellular environment which can be optically interrogated and detected within the cell itself or from an indicator compound, for example, a fluorophore, chromophore or dye, either attached to the cell, taken up in the cell, or added to the local cell environment. The biosensor of the present invention thus capitalizes on the ability of living cells to respond to biologically significant compounds. Since the selectivity of living cells for such compounds has considerable value and utility in drug screening and analysis of complex biological fluids, the biosensor of the present invention offers distinct advantages to high throughput screening of combinatorial libraries where hundreds of thousands of candidate compounds must be evaluated.

As will be appreciated by one skilled in the art, a variety of substrate materials and substrate configurations may be employed with the biosensor array of the present invention. Any substrate or material that can be adapted to provide discrete sites that are appropriate for the attachment or association of individual cells and is accessible for optical interrogation of the cell array and detection of cell responses would be particularly useful as an array substrate. Candidate substrate materials include, but are not limited to, glasses, polymers, ceramics, metals, and composites formed from these materials. Substrate surface geometries may be planer, spherical, concave, convex, and textured. Preferably, a suitable substrate would be configured so as to provide for optical interrogation of the array and detection of cell responses to analytes of interest.

In a preferred embodiment, the biosensor array of the present invention is incorporated into a fiber optic array which serves as a substrate for cell placement. By "fiber optic array" or other grammatical equivalents herein is meant a plurality of individual fibers or fiber strands that may be either grouped together as discrete, individual fibers in a fiber bundle or, alternatively, joined along their axial dimensions as a preformed unitary fiber optic array. The individual fibers in such an array may be arranged in a uniform or coherent configuration, for example as in an imaging fiber, or may be randomly oriented and incoherent. When a fiber optic array is employed as a sensor substrate, the distal end of each fiber in a fiber optic bundle or fiber optic array is chemically etched so as to create a cavity or microwell. A schematic diagram of the biosensor array concept of the present invention is shown in FIG. 1. In a preferred embodiment, individual living cells of either a monoculture of cells or mixed populations of cell lines are deployed in the microwells. The microwells are formed by anisotropic etching of the cores of the individual fiber in the fiber bundle or fiber array. The microwells are formed by controlling the etching process so as to remove a centralized core portion of the individual fiber strands while leaving the surrounding cladding intact. The resultant etched cavity is dimensioned for accommodating an individual cell. By selecting a fiber optic bundle or fiber optic array whose individual fiber cores are appropriately sized and by careful control of the etching conditions, the diameter and depth of the microwells can be controlled and adjusted over any convenient dimension range so as to match the size of any desired cell type.

In one embodiment, either discrete substrate cites or the interior surfaces of the microwells may be coated with a thin film of biologically compatible material such as collagen, fibronectin, polylysine, polyethylene glycol, polystyrene, or a metal such as gold, platinum or palladium. In an alternative embodiment, an indicator compound, for example, a fluorophore, a chromophore or dye, may be attached to the microwell surface for detecting cell responses to chemical or biological stimulation.

By incorporating a biosensor into an optically interrogatable substrate or a fiber optic array, the innovation of the biosensor of the present invention is in providing for optical coupling of individual cells located at discrete substrate cites or microwells with discrete detector elements, CCD cameras, or individual optical fibers in a fiber optic array or bundle that are in optical communication with such devices. By "optical coupling", "optical communication", or "optical cooperation" or other grammatical equivalents herein is meant the capability of either optically stimulating individual cells within the biosensor array with excitation light or optically interrogating the optical response of individual cells within the array to analytes, by conveying light to and from individual cells located at discrete cites within the array using either conventional optical train elements or optical fibers. Since typical fiber optic arrays contain thousands of discrete individual fiber strands, the invention thus provides for the individual optical coupling and interrogation of thousands of cells within an array, thereby providing for a large number of independent cell response measurements for each cell population within an array. Due to both the number of cell populations available and the correspondingly large number of individual cells within each cell population, a significant innovation of the present invention is in providing for the summing and amplification of the characteristic optical response signatures of multiple independent measurements taken from cells within each cell population, thereby improving the detection limit and sensitivity of the biosensor.

An additional innovation of the present invention is that, by deploying a large number of cell populations within the array, and providing a large number of individual cells in each population, the discriminating capabilities of the biosensor array toward biological or chemical analytes is significantly enhanced by providing for thousands of cell responses from a large number of cell populations. This feature directly mimics the actual behavior of the human olfactory system where the combined signals from thousands of receptor cells, in each grouping of nearly a thousand different receptor cell types found in the epithelium layer, none of which are particularly sensitive in themselves, lead to a highly amplified sensory response to odors [see Kauer, et al, *Trends Neurosci.* 14:79(1991). One embodiment of the present invention thus mimics the evolutionary scent amplification process found in the human olfactory system in order to significantly enhance biosensor array sensitivity to analytes by summing the low-level responses of a large number of cells in the biosensor array. By summing the responses from a number of cells at low analyte concentrations, a substantial improvement in signal-to-noise ratio can be achieved and a corresponding reduction in the detection limit of the biosensor array is obtained.

A unique feature of the biosensor array of the present invention is that each of the individual cells and cell populations in the array may be encoded for maintaining cell type identity and location where randomly mixed populations of cells are employed. Cells may be encoded prior to disposing them in the microwells or, alternatively, following placement in the microwells. The invention provides for either encoding randomly mixed individual cells and cell populations with a fluorophoric or chromophoric dye compound or, alternatively, using self-encoded cells which are either naturally fluorescing or genetically engineered to fluoresce. Although cell populations may be randomly mixed together, this innovative feature provides for the identity and location of each cell type to be determined via a characteristic optical response signature when the cell array is either illuminated by excitation light energy or, alternatively, subjected to biological stimuli.

In one embodiment, cells or cell populations may be self-encoded by selecting cell populations, such as green fluorescent protein mutants, which exhibit either chemiluminescence, bioluminescence, or whose optical response to biological stimuli yield a unique detectable fluorescence signal. Other cell populations may be employed where cells within a population yield a unique temporal optical response to stimuli. Either naturally occurring of genetically engineered cell lines may be utilized.

In various alternative embodiments, cells may be encoded with dye compounds which are attached to cells, taken up by cells or provided in the local cell environment. Examples of useful encoding dyes include fluorophores, chromophores, stains or a dye compounds. For example, conventional cell fluorophore probes such as fluoresceins, rhodamines, naphthalimides, phycobiliproteins, nitrobenzoxadiazole may be utilized. A particularly useful reference for selecting appropriate encoding dyes is R. P. Haugland, *Handbook of Fluorescent Probes and Research Chemicals* (6$^{th}$ ed.), Molecular Probes Inc.(Eugene, Oreg., 1996) which is herein incorporated by this reference.

When dye compounds are employed for encoding, cell populations within the biosensor array may be readily decoded by exciting the array with excitation light and indexing cells types within randomly dispersed populations by their response to excitation. In one embodiment, a single fluorophoric or chromophoric material or dye is used for encoding the cells. In an alternative embodiment, two or more encoding materials or dyes may be used to encode cell populations and the optical response intensity ratios for the dyes, produced by exposure to excitation light energy, are employed to encode and identify members of the cell population with the array. In an alternative embodiment, cells may be decoded by excitation light when exposed to a common analyte. In another embodiment, encoded cells may be decoded by their response to a generic cell activator using either a pH or $Ca^{+2}$ indicator.

The innovative cell encoding feature of the present invention overcomes certain limitations of prior art devices by eliminating the need for mechanically scanning the array, mechanically indexing the location of cells, and mechanically positioning the array for measurements of individual cells within the array. The invention thus provides for rapid, simultaneous measurements of all cells and cell populations within the array without the need to mechanically scan the array to acquire a series of sequential measurements for each cell. Thus monitoring and measuring the responses of all cells in the array occurs simultaneously without a prolonged delay between the first cell measurement and last cell measurement. The ability to measure all cell responses simultaneously thus provides for the capability to monitor both short term cell response and long term cell response.

This innovative feature thus enables the monitoring of rapid biologically significant cell processes and cell responses on a short time scale. In addition, the ability to simultaneously measure cell responses over a short time scale enables the measurement of individual cell and cell population response rates to changes in the biosensor array environment. This feature thus provides for additional discriminating response information which is useful for detecting biological or chemical analytes.

The biosensor array of the present invention can employ either naturally occurring cells and cell populations or genetically engineered cell lines. Virtually any cell type and size can be accommodated by matching the cell size to individual optical fiber optic core diameters and etching conditions. In one embodiment, NIH 3T3 mouse fibroblast cells were employed. In alternative embodiments, other cells types such as *E. coli* bacteria, staphylococcus bacteria, myoblast precursors to skeletal muscle cells, neutrophil white blood cells, lymphocyte white blood cells, erythroblast red blood cells, osteoblast bone cells, chondrocyte cartilage cells, basophil white blood cells, eosinophil white blood cells, adipocyte fat cells, invertebrate neurons (*Helix aspera*), mammalian neurons, or adrenomedullary cells, may be utilized as well. Any cell type or mixtures of cell population types may also be employed providing the microwell can accommodate the individual cell size.

The optical responses of individual cells and cell populations to chemical or biological stimuli are typically interrogated and detected by coupling individual cells with appropriate indicators which may be either fluorophores, chromophores, stains or a dye compounds. For example, conventional cell fluorophore probes such as fluoresceins, rhodamines, naphthalimides, phycobiliproteins, nitrobenzoxadiazole may be utilized. Alternatively, permeant or impermeant cell membrane potential indicators, ion indicators, reactive oxygen indicators and pH indicators may be employed. A particularly useful reference for selecting appropriate indicators is R. P. Haugland, *Handbook of Fluorescent Probes and Research Chemicals* (6$^{th}$ ed.), Molecular Probes Inc.(Eugene, Oreg., 1996) which is herein incorporated by this reference. Any suitable indicator or combinations of indicators may be utilized provided the indicator does not compromise cell response. In a variety of alternative embodiments, indicators may be either incorporated directly into the cell, for example by attachment to the cell membrane, by absorption or injection into the cell cytoplasm, or added to the cell external environment, such as a fluid contained within the microwells. In an alternative embodiment, indicators may be attached to the surface of the microwells.

Individual cells or arrays of cells and cell populations may be optically interrogated and cell responses to analytes may be measured by conventional optical methods and instrumentation that are known to those skilled in the art. Cells may be optically interrogated with any suitable excitation light energy source, such as arc lamps, lasers, or light emitting diodes, that are capable of producing light at an appropriate wavelength for exciting dye indicators that may be employed for encoding cell populations or for responding to analytes of interest. The optical responses of individual cells or cell populations may be monitored and measured with any suitable optical detection means, including, but not limited to film or conventional optical detectors, such as photoresistors, photomultiplier tubes, photodiodes, or charge coupled device (CCD) cameras. In a preferred embodiment, CCD cameras are employed to capture fluorescent images of the biosensor array for detecting responses of each cell and various cell subpopulations to analytes. In this embodiment, both individual cell responses and a captured image of the array response may be employed for detecting analytes.

In summary, the biosensor array and sensing method of the present invention offers many distinct advantages in overcoming the limitations of prior art devices. The sensor arrays are easily fabricated from commercially available optical imaging fibers to yield a cost effective, high density, precisely formed, biosensor array without requiring any sophisticated machining or forming process. Since optical fibers and fiber optic arrays are available in a wide variety of fiber core diameters, most cell types and sizes may be accommodated in by the device and method of the present invention. In addition, cells can be readily dispersed into the microwell array in random fashion with no need for physical indexing or scanning to locate individual cells or cell populations due to the innovative cell encoding technique. Sensing methods and sensing systems which employ the biosensor and sensor array of the present invention avoids many of the limitations in manipulating cells encountered with prior art devices. Once cells are placed within the microwells of the array, conventional imaging systems and methods which employ an imaging camera and conventional optics, can monitor the response of thousands of cells simultaneously, eliminating requirements for mechanical scanning mechanisms. Analysis of measurement data is further facilitated by implementing commercially available imaging software to process images of the biosensor array using pattern recognition techniques combined with neural network and other statistical methods.

The biosensor array and sensing method of the present invention may be employed for a number of useful analytical applications where individual cells, which are chemically or biologically stimulated by the presence of a biological or chemical material in the local cell environment, will respond to their environment by producing an optically detectable response either due to the presence of an appropriate indicator or due to the characteristic optical response of particular cell types which exhibit either natural or genetically-engineered chemiluminescence or bioluminescence. The biosensor array and method of the present invention thus capitalizes on the ability of living cells to respond to biologically significant compounds. Since the selectivity of living cells for such compounds has considerable value and utility in drug screening and analysis of complex biological fluids, the biosensor of the present invention offers distinct advantages to high throughput screening of combinatorial libraries where hundreds of thousands of candidate compounds must be evaluated.

The above and other features of the invention, including various novel details of construction and methods, and other advantages, will now be more particularly described with reference to the accompanying drawings and claims. It will be understood to one skilled in the art that the particular apparatus and method embodying the invention are shown by way of illustration and not as a limitation of the invention. The principles and features of the invention may be employed in various and numerous embodiments without departing from the scope of the invention.

BRIEF DESCRIPTION OF THE DRAWINGS

The invention is pointed out with particularity in the appended claims. Other features and benefits of the invention can be more clearly understood with reference to the specification and the accompanying drawings in which:

FIG. 1 is a schematic diagram of the biosensor array concept of the present invention;

FIGS. 2a–b are atomic force microscope photomicrographs of a microwell array used in a biosensor array of the present invention;

FIG. 3 is a schematic diagram of the method for depositing cells in microwells used for a biosensor array of the present invention;

FIG. 4 is an SEM photomicrograph of a single NIH 3T3 mouse fibroblast cell in a microwell;

FIG. 5 is a schematic representation of a method for establishing cell viability of cell populations within the biosensor array of the present invention;

FIG. 6 is a characteristic fluorescence image pattern identifying the location of a cells which test positively for cell viability in a biosensor array of the present invention;

FIG. 7 shows the temporal response of the combined fluorescence intensity of the viable cell population identified in FIG. 6;

FIG. 8 is a fluorescence optical image of an encoded cell population within a biosensor array of the present invention;

FIG. 9 is a schematic block diagram of the measurement system used for optical measurements of the microwell sensor array;

FIG. 10 is a plot of average BCECF fluorescence for nine biosensor array cells over time; and FIGS. 11a–b compares the viability of cells inserted in microwells both with and without a pretreatment for filling the microwells with culture media.

DETAILED DESCRIPTION OF THE PREFERRED EMBODIMENTS

A. Fabrication of Microwell Arrays

The present invention provides array compositions comprising at least a first substrate with a surface comprising individual sites. By "array" herein is meant a plurality of cells in an array format; the size of the array will depend on the composition and end use of the array. Arrays containing from about 2 different cells to many millions can be made, with very large fiber optic arrays being possible. Generally, the array will comprise from two to as many as a billion or more, depending on the size of the cells and the substrate, as well as the end use of the array, thus very high density, high density, moderate density, low density and very low density arrays may be made. Preferred ranges for very high density arrays are from about 10,000,000 to about 2,000,000,000 (all numbers herein are per cm2), with from about 100,000,000 to about 1,000,000,000 being preferred. High density arrays range about 100,000 to about 10,000,000, with from about 1,000,000 to about 5,000,000 being particularly preferred. Moderate density arrays range from about 10,000 to about 100,000 being particularly preferred, and from about 20,000 to about 50,000 being especially preferred. Low density arrays are generally less than 10,000, with from about 1,000 to about 5,000 being preferred. Very low density arrays are less than 1,000, with from about 10 to about 1000 being preferred, and from about 100 to about 500 being particularly preferred. In some embodiments, the compositions of the invention may not be in array format; that is, for some embodiments, compositions comprising a single cell may be made as well. In addition, in some arrays, multiple substrates may be used, either of different or identical compositions. Thus for example, large arrays may comprise a plurality of smaller substrates.

In addition, one advantage of the present compositions is that particularly through the use of fiber optic technology, extremely high density arrays can be made. Thus for example, because cells frequently may be 200 fm or less and very small fibers are known, it is possible to have as many as 250,000 or more (in some instances, 1 million) different fibers and cells in a 1 mm2 fiber optic bundle, with densities of greater than 15,000,000 individual cells and fibers (again, in some instances as many as 25–50 million) per 0.5 cm2 obtainable.

By "substrate" or "solid support" or other grammatical equivalents herein is meant any material that can be modified to contain discrete individual sites appropriate for the attachment or association of cells and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluorescese.

Generally the substrate is flat (planar), although as will be appreciated by those in the art, other configurations of substrates may be used as well; for example, three dimensional configurations can be used, for example by embedding the cells in a porous block of plastic that allows sample access to the cells and using a confocal microscope for detection. Similarly, the cells may be placed on the inside surface of a tube, for flow-through sample analysis to minimize sample volume. Preferred substrates include optical fiber bundles as discussed below, and flat planar substrates such as glass, polystyrene and other plastics and acrylics.

In a preferred embodiment, the substrate is an optical fiber bundle or array, as is generally described in U.S. Ser. Nos. 08/944,850 and 08/519,062, PCT US98/05025, and PCT US98/09163, all of which are expressly incorporated herein by reference. Preferred embodiments utilize preformed unitary fiber optic arrays. By "preformed unitary fiber optic array" herein is meant an array of discrete individual fiber optic strands that are co-axially disposed and joined along their lengths. The fiber strands are generally individually clad. However, one thing that distinguished a preformed unitary array from other fiber optic formats is that the fibers are not individually physically manipulatable; that is, one strand generally cannot be physically separated at any point along its length from another fiber strand. In general, the discussion herein is focused on fiber optic arrays, although as will be appreciated by those in the art, other substrates as described above may be used in any embodiment described herein.

At least one surface of the substrate is modified to contain discrete, individual sites for later association of cells. These sites may comprise physically altered sites, i.e. physical configurations such as wells or small depressions in the substrate that can retain the cells, such that a cell can rest in the well, or the use of other forces (magnetic or compressive), or chemically altered or active sites, such as biologically or chemically functionalized sites, electrostatically altered sites, hydrophobically/hydrophilically functionalized sites, spots of adhesive, etc.

The sites may be a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of cells on the substrate. However, it should be noted that these sites may not be discrete sites. That is, it is possible to use a uniform surface of adhesive or chemical functionalities, for example, that allows the attachment of cells at any position. That is, the surface of the substrate is modified to allow attachment of the cells at individual sites, whether or not those sites are contiguous or non-contiguous with other sites. Thus, the surface of the substrate may be modified such that discrete sites are formed that can only have a single associated cell, or alternatively, the surface of the substrate is modified and cells may go down anywhere, but they end up at discrete sites.

In a preferred embodiment, the surface of the substrate is modified to contain microwells, i.e. depressions in the surface of the substrate. This may be done as is generally known in the art using a variety of techniques, including, but not limited to, photolithography, stamping techniques, pressing, casting, molding, microetching, electrolytic deposition, chemical or physical vapor deposition employing masks or templates, electrochemical machining, laser machining or ablation, electron beam machining or ablation, and conventional machining. As will be appreciated by those in the art, the technique used will depend on the composition and shape of the substrate.

In a preferred embodiment, physical alterations are made in a surface of the substrate to produce the sites. In a preferred embodiment, the substrate is a fiber optic bundle and the surface of the substrate is a terminal end of the fiber bundle, as is generally described in Ser. Nos. 08/818,199 and 09/151,877, both of which are hereby expressly incorporated by reference. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the cells to be added to the wells.

Generally in this embodiment, the cells are non-covalently associated in the wells, although the wells may additionally be biologically or chemically functionalized as is generally described below, cross-linking agents may be used, or a physical barrier may be used, i.e. a film or membrane over the cells.

In a preferred embodiment, the surface of the substrate is modified to contain biologically or chemically modified sites, that can be used to attach, either covalently or non-covalently, the cells of the invention to the discrete sites or locations on the substrate. "Chemically modified sites" in this context includes, but is not limited to, the addition of a pattern of chemical functional groups including amino groups, carboxy groups, oxo groups and thiol groups, that can be used to attach cells which generally also contain corresponding reactive functional groups on their surfaces; the addition of a pattern of adhesive that can be used to bind the cells, (either by prior chemical functionalization for the addition of the adhesive or direct addition of the adhesive); the addition of a pattern of charged groups (similar to the chemical functionalities) for the electrostatic attachment of the cells, i.e. when the cells comprise charged groups opposite to the sites; the addition of a pattern of chemical functional groups that renders the sites differentially hydrophobic or hydrophilic, such that the addition of similarly hydrophobic or hydrophilic cells under suitable experimental conditions will result in association of the cells to the sites on the basis of hydroaffinity. Alternatively, biological modifications include the use of binding ligands or binding partner pairs, including, but not limited to, antigen/antibody pairs, enzyme/substrate or inhibitor pairs, receptor-ligand pairs, carbohydrates and their binding partners (lectins, etc.).

In a preferred embodiment, an array of micrometer-sized wells is created at the distal face of an optical imaging fiber by a selective etching process which takes advantage of the difference in etch rates between core and cladding materials. This process has been previously disclosed by Pantano, et al., *Chem. Mater.* 8:2832 (1996), and Walt, et al., in U.S. patent application Ser. No. 08/818,199. The etch reaction time and conditions are adjusted to achieve desired control over the resultant microwell size and volume. Microwells are thus sized to accommodate a single cell of any desired cell type.

The sensor array design can accommodate a variety of cell sizes and configurations utilizing either commercially available optical fibers and fiber optic arrays or custom made fibers or fiber arrays.

The major requirement in selecting candidate fibers or fiber optic arrays for fabricating sensors is that the individual fibers have etchable cores.

In one embodiment, the interior surfaces of the microwells may be coated with a thin film or passivation layer of biologically compatible material, similar to the biological modifications of the substrate as outlined above. For example, materials known to support cell growth or adhesion may be used, including, but not limited to, fibronectin, any number of known polymers including collagen, polylysine and other polyamino acids, polyethylene glycol and polystyrene, growth factors, hormones, cytokines, etc. Similarly, binding ligands as outlined above may be coated onto the surface of the wells. In addition, coatings or films of metals such as a metal such as gold, platinum or palladium may be employed. In an alternative embodiment, an indicator compound, for example, a fluorophore, a chromophore or dye, may be attached to the microwell surface for detecting cell responses to chemical or biological stimulation.

The method of fabricating microwells can be adapted to any fiber size so as to accommodate a wide range of cell sizes for incorporation into appropriately sized microwells. For example, optical fibers having core diameters ranging from 1.6 to 100 um are commercially available from either Galileo Electro-Optics Corp. (Sturbridge, Mass.) or Edmund Scientific (Barrington, N.J.). In addition, larger sizes are available by custom order. Thus, appropriately sized fibers can be utilized to study such diverse cell sizes as *E. coli,* with a typical cell dimension of 0.7 to 1.5 um, and mammalian neurons, with a cell dimension of up to 150 um.

In one embodiment, a fiber optic array, having a 1 mm outer diameter and 7 um individual fiber core diameters, available from Galileo Electro-Optics Corp. (Sturbridge, Mass.), was utilized. One end of the fiber optic array was polished using a series of aluminum oxide lapping films 12, 9, 3, 1, 0.3 um available from Mark V Lab (East Granby, Conn.). The fibers were then sonicated for approximately 1 minute to remove any residue from the polishing procedure. The etching procedure was performed by submerging the distal face of the fiber at a right angle in 700 uL of a buffered hydrofluoric acid solution, comprising 100 uL hydrofluoric acid (50%), 0.2 g ammonium fluoride, and 600 uL of deionized water, for approximately 65 seconds. The fiber was then rinsed with deionized water and sonicated for 1 minute to remove any salts that may have been formed during the etching procedure. In this embodiment, the etch reaction time was tailored such that the well size was 7 microns in diameter, 3 microns in depth, and approximately 90 fL in volume. Both scanning electron microscopy (SEM) and atomic force microscopy (AFM) may be utilized to characterize etched microwells. In FIG. 2a, a typical microwell array formed by the etching procedure is shown in an AMF photomicrograph (Digital Instruments Nanoscope IIIa, Santa Barbara, Calif.). In FIG. 2, an oblique view of the microwell array is provided. As shown in these figures, the microwells formed by this process are extremely uniform due to the uniform characteristic structure of the fiber optic array.

B. Selection of Cell Types

Virtually any cell type and size can be accommodated in fabricating the sensor of the present invention by matching the cell size to individual optical fiber optic core diameters. Virtually any naturally occurring or genetically engineered (i.e. containing exogeneous nucleic acid) eukaryotic or procaryotic cell type may be used, with plants, invertebrates, bacteria and mammalian cells, including, but not limited to, green fluorescent protein mutants, primate, rodent and human cells and cell lines being preferred, as well as mixtures of cell types.

In one embodiment, NIH 3T3 mouse fibroblast cells were employed. These cells are typically 15–20 um in size. Other cells types such as *E. coli* bacteria, 1×3 um, staphylococcus bacteria, approximately 1 um, myoblast precursors to skeletal muscle cells, 15–20 um, neutrophil white blood cells, 10 um, lymphocyte white blood cells, 10 um, erythroblast red blood cells, 5 um, osteoblast bone cells, 15–20 um, chondrocyte cartilage cells, 15–20 um, basophil white blood cells, 10 um, eosinophil white blood cells, 10 um, adipocyte fat cells, 20 um, invertebrate neurons (*Helix aspera*), 125 um, mammalian neurons, 4–140 um, or adrenomedullary cells, 13–16 um, melanocytes, 20 um, epithelial cells, 20 um, or endothelial cells, 15–20 um, may be utilized as well. Additional other suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells, osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, COS, etc. A particularly useful source of cell lines may be found in *ATCC Cell Lines and Hybridomas* ($8^{th}$ ed., 1994), *Bacteria and Bacteriophages* ($19^{th}$ ed., 1996), *Yeast* (1995), *Mycology and Botany* ($19^{th}$ ed., 1996), and *Protists: Algae and Protozoa* (1 $8^{th}$ ed., 1993), available from American Type Culture Co. (Rockville, Md.), all of which are herein incorporated by reference.

C. Dispersion of Cells in Microwells

Once the microwell size is tailored to accommodate specific cell sizes, the next step in creating an array of cells is to randomly disperse cells into the microwells. FIG. 3 is a schematic diagram showing the method for dispersing and depositing cells in the microwell array. Cell populations are conventionally cultured with growth media which matches cell needs. Culture media is formulated according to either recipes provided by cell line providers, journal articles or reference texts. A particularly useful reference for media preparation is *ATCC Quality Control Methods for Cell Lines* ($2^{nd}$ ed.), American Type Culture Co. (Rockville, Md.) which is herein incorporated by reference. After culturing, cells are typically trypsinized using aseptic techniques to remove them from the cell culture dish and suspend them in growth media.

In one embodiment, NIH 3T3 mouse fibroblast cells, available from American Type Culture Collection (Rockville, Md.) were utilized. The cells were randomly dispersed into the wells by removing the adhered cells from the culture dish with a proteolytic enzyme, such as Trypsin-EDTA (0.05% Trypsin, 0.53 mM EDTA.4Na), available from; Gibco BRL (Grand Island, N.Y.], using aseptic techniques and placing the cells into a single-cell suspension in growth media, such as Dulbecco's Modified Eagle Medium with 1% PenicillinStreptomycin, 1% L-Glutamine-200 mM, and 10% fetal calf serum, available from Gibco BRL.

To disperse cells into the wells, approximately 1.5 ml of the cell suspension was concentrated by centrifugation at 2000 RPM for 3.5 minutes. The supernatant is drawn off and the centrifuge tube was tapped to resuspend the cells. The cell suspension was then added to a 1.5 mm diameter capillary tube. Prior to adding cells to the microwell array, the end of the fiber optic array which contains the microwells was sonicated under vacuum in cell media for approximately 15 minutes to flush and fill the microwells with media. The microwell end of the fiber was then inserted into the capillary tube and secured in place with a thin strip of laboratory film. The capillary tube/fiber set-up was then incubated in the vertical position for 1–2 hours allowing the suspended cells to settle into the wells and adhere to the well bottom. The length of time required to fill the microwells is dependent only on the amount of time required for the cells to adhere to the microwell bottom. Excess cells which were not accommodated by a well were wiped away with a cotton swab wet with growth media. FIG. 4 is an SEM photomicrograph of a single cell dispersed in an etched microwell.

Once they are positioned within the microwells, cells with typically attach to microwell surfaces within 1–2 hours by protein contact. Cell culture media in the microwells may be periodically replenished by exposing the distal surface of the fiber optic array to fresh media and allowing nutrients to diffuse into the microwell cavities. Typically, cells will divide every twelve to fifteen hours. While the size of the microwells tends to confine individual cells, the array will accommodate limited cell splitting over time. Microwell volume will restrict cell splitting due to the well know cell phenomenon of contact inhibition when cells are touching.

D. Establishing Cell Viability

In one embodiment, the cell viability in the wells was investigated using a pH indicator, 2'-7'-bis-(2carboxyethyl)-5-(and-6-)-carboxyfluorescein (BCECF-AM) which has an excitation wavelength of 505 nm and an emission wavelength of 535 nm and is available from Molecular Probes (Eugene, Oreg.). The acetoxymethyl (AM) ester form of BCECF is non-fluorescent in solution. The BCECF-AM is cell membrane permeant and passively enters the cell where, once inside the cell, the lipophilic blocking groups are cleaved by non-specific esterases resulting in an increase in fluorescent intensity. This increase in fluorescent intensity is indicative of the cell viability. FIG. 5 is a schematic representation of one embodiment of a method used for establishing cell viability in a sensor array.

For viability tests, an array of encoded cells previously dispersed in microwells was immersed in a 1 uM solution of BCECF-AM for 1 minute. The cell array was removed and rinsed thoroughly to remove any residual dye. Fluorescent images of cell responses were acquired every 30 seconds using a 1.0 second acquisition time to monitor the increase in fluorescent intensity due to the pH of healthy cells. Prior to viability measurements, a cell location template was generated through excitation of the encoded cells, using the encoding method described herein, and the locations of individual cells was superimposed on viability measurement images in order to identify the location of healthy cells within the array. A fluorescence image of the encoded cells is shown in FIG. 6. In FIG. 7, the fluorescent intensity response of the cells indicates a gradual increase as the lipophilic groups are cleaved from the BCECF-AM dye within the cell. The fluorescent intensity response of the wells which do not contain cells was negligible.

In a alternative embodiment, BCECF-Dextran, available from Molecular Probes, was used for cell viability measurements. A 0.1 uM solution of the dye was added to cell media contained within array microwells. BCECF requires excitation at two wavelengths, 490 nm and 440 nm, and the ratio of the emitted light intensity at 530 nm for each wavelength is proportional to pH. This dye is conjugated with a large Dextran group to prevent-entry into the cell through the cell membrane. Thus, BCECF-Dextran can monitor decreases in pH within the external cell environment due to cell metabolism. FIG. 10 shows the average response of nine cells over time where the pH of the cell environment gradually decreases due to cell metabolism.

In another embodiment a commercial cell viability assay, LIVE/DEAD® from Molecular Probes (Eugene, Oreg.), was employed. This assay provides a two-color fluorescence cell viability assay based on intracellular esterase activity and plasma membrane integrity. Live cells are distinguished by the enzymatic conversion of the cell-permeant non-fluorescent calcein AM to fluorescent calcein, with an excitation wavelength at 495 nm and an emission wavelength at 515 nm. Dead cells are distinguished by binding ethidium homodimer (EthD-1), with an excitation wavelength at 495 nm and an emission wavelength at 635 nm, to nucleic acids which is accompanied by a 40-fold increase in fluorescent intensity. EthD-1 is excluded by the intact plasma membranes of living cells. Background fluorescence levels are inherently low with this assay technique because the dyes are virtually non-fluorescent before interacting with cells.

In a typical procedure, a working solution of 2 uM calcein AM and 4 uM EthD-1 was prepared in serium-free medium. An array of NIH 3T3 mouse fibroblast cells was cultured at the distal face of a microwell array. The proximal face of the imaging fiber was focused on the imaging system. The cell array at the distal face of the imaging fiber was placed in serium-free medium without dye. The cell array was excited at 495 nm and emission values from a population of 25 cells were acquired for 300 ms at 515 nm (Live) and 635 nm (Dead). These values serve as background reading for these measurements. The cell array was then placed in the dye solution and the cell array was excited at 495 nm and emission values from 25 cells were acquired for 300 ms at 515 nm (Live) and 635 nm (Dead) every minute for 30 minutes. All measurements were performed at room temperature. Average fluorescent intensity for the live and dead cell wavelengths are plotted versus time after subtracting the background fluorescence measurement at each emission wavelength.

This assay was used to evaluate pretreatment methods for filling the microwells of a biosensor array with culture media prior to inserting cells. By comparing the viability of cells placed in microwells after various treatments, it was determined that, in a preferred embodiment, sonicating the mircrowell array under vacuum for 15 minutes prior to insertion of cells improves viability by ensuring that the microwells are filled with culture media. In FIG. 11a, the average fluorescent intensity for dead cells and live cells is plotted with time where no pretreatment was utilized. In FIG. 11b, results are plotted for a pretreated microwell array. Comparison of the two figures demonstrates the advantage of prefilling the microwells with culture media prior to cell insertion. In this example, when the microwell array was not sonicated prior to adding the cells the cells displayed immediate cell death. In this example, when the microwells were sonicated under vacuum to fill the arrays with culture media, the cells remained viable for approximately 20 minutes.

E. Encoding Cell Populations

A unique feature of the biosensor array of the present invention is that cells within each cell population are individually encoded for maintaining cell identity within the array when randomly mixed populations of cells are employed. Cells may be encoded with a single fluorophore or chromophore dye or ratios of such dyes. Alternatively, cells may be encoded by either injecting a non-toxic fluorescing compound into the cell cytoplasm or by employing natural or genetically-engineered cells lines which exhibit chemiluminescence or bioluminescence, such as green fluorescent protein mutants. Although a plurality of cell populations may be randomly mixed in the biosensor array, the identity and location of each cell type is determined via a characteristic optical response signature when the array is illuminated by excitation light energy. Cells may be encoded prior to disposing them in the microwells or, alternatively, following placement in the microwells. In one embodiment, a single fluorophoric or chromophoric material or dye is used for encoding the cells. In an alternative embodiment, two or more encoding materials or dyes may be used to encode cell populations and the ratio of the optical response light intensity from each material or dye, produced by exposure to excitation light energy, is used to identify the positions of individual cells within the cell population and locate them in the array. In various alternative embodiments, cells may be encoded with dye compounds which are attached to cells, taken up by cells or provided in the local cell environment.

A wide variety of fluorophores, chromophores, stains or a dye compounds may be used for encoding cells. Encoding dyes may be permeant or impermeant to the cell membrane. Impermeant dyes may be conjugated with acetoxymethyl ester to allow take up by cells. In one embodiment, conventional conjugate or reactive cell membrane stains, cell tracers, or cell probes such as fluoresceins, rhodamines. eosins naphthalimides, phycobiliproteins, nitrobenzoxadiazole may be utilized. In other embodiments, cyanine dyes, such as SYTO® (Molecular Probes), amine-reactive dyes, thiol-reactive dyes, lipopilic dyes, and DNA intercalators, such as acridine orange, may be employed. In one embodiment, fluorogenic or chromogenic enzyme substrates may be taken up by the cells, processesed by intracellular enzymes, such as glycosidases, phosphatases, luciferase, or chloramphenicol acetyltransferase, and provide encoding for cell populations. In an alternative embodiment, cell organelle dye probes may be employed for encoding. In one embodiment, cell membrane probes such as carbocyanines and lipophilicaminostyrls may be utilized for encoding.

By way of example, Tables 1 and 2 provide a partial listing of a various types of dyes and their corresponding excitation and emission wavelengths which have utility for encoding cell populations in sensor arrays of the present invention. In addition, a particularly useful reference for selecting other types of encoding dyes is R. P. Haugland, *Handbook of Fluorescent Probes and Research Chemicals* ($6^{th}$ ed.), Molecular Probes Inc.(Eugene, Oreg., 1996).

Cell encoding eliminates the need for mechanically scanning the array, mechanically indexing the location of cells, and mechanically positioning the array for measurements of individual cells. In addition, by encoding all cells within the array, simultaneous measurements of the entire array are possible since the responses of individual cells are readily associated with a specific cell population type because each cell is encoded. Encoding of cells thus provides for rapid, simultaneous measurements of all cells and cell populations within the array without the need to mechanically scan the array to acquire a series of sequential measurements for each cell. Since monitoring and measuring the responses of all cells in the array occurs simultaneously, without a prolonged delay between the first cell measurement and last cell measurement, the biosensor array of the present invention provides the capability to monitor both short term and long term cell responses to biological stimuli. The biosensor array of the present invention thus has the unique ability for measuring both cell responses and response rates to analytes. This feature provides

TABLE 1

1. Plasma Membrane Stains
PKH22 green fluorochrome  551ex/567em
PHK67 green fluorochrome  490ex/502em
PKH26 red fluorochrome  551ex/567em
lipophilic carbocyanines
    DiI - orange fluorescence
    DiO - green fluorescence
    DID - red flurescence
    FM 1-43 - green fluorescence 510ex/626em
    FM 4-64 - red fluorescence 515ex/640em
    RH 414 - orange fluorescence 532ex/716em
lipophilic dextrans
    tetramethylrhodamine dextrans (10,000 MW) 470ex/500em
    fluorescein dextran (10,000 MW) 495ex/530em
2. Tracker Probes
Blue 7-amino-4-chloromethyl coumarin 354ex/466em
4-chloromethyl-6,8-difluoro-7-hydroxy coumarin 371 ex/464em
4-chloromethyl-7-hydroxy coumarin 372ex/470em
Green 5-chloromethyl fluorescein diacetate 492ex/516em
8-chloromethyl BODIPY 522ex/528em
Yellow-Green
5-chloromethyleosin diacetate 524ex/544em
Orange
5-(and 6)-(((4-chloromethyl)benzoyl)amino) tetramethylrhodamine 540ex/566em
3. Amine-Reactive Probes
fluorescein isothiocyanate 494ex/519em
carboxyfluorescein succinimidyl esters 504ex/529em
carboxyeosin succinimidyl esters 492ex/517em

TABLE 2

Molecular Probes' organelle-selective probes

| Blue Fluorescent and Nonfluorescent Probes | | Green Fluorescent Probes | | Yellow and Orange Fluorescent Probes | |
|---|---|---|---|---|---|
| Cat # | Probe | Cat # | Probe | Cat # | Probe |
| Probes for Mitochondria -- see Section 12.2 | | | | | |
| L-6868 | Lucigenin † | A-1372 | Nonyl acridine orange | D-288 | 4-Di-1-ASP (DASPMI) |
| | | D-273 | $DiOC_6(3)$ | D-308 | 2-Di-I-ASP (DASPMI) |
| | | D-303 | $DiOC_2(5)$ | D-426 | DASPEI |
| | | D-378 | $DiOC_7(3)$ (for plant mitochondria) | M-7510 | MitoTracker Orange CMTMRos* |
| | | M-7502 | MitoFluor Green | R-634 | Rhodamine 6G |
| | | M-7514 | MitoTracker Green FM* | R-648 | Rhodamine B, hexyl ester |
| | | R-302 | Rhodamine 123 | T-639 | Tetramethylrosamine |
| | | S-7529 | SYTO 18 yeast mitochondrial stain | T-668 | Tetramethylrhodamine, methyl ester |
| | | T-3168 | JC - 1 ‡ | T-669 | Tetramethylrhodamine, ethyl ester |
| Probes for Mitochondria (Probes Requiring Intracellular Oxidation) -- see Section 12.2 | | | | | |
| | | D-632 | Dihydrorhodamine 123 | D-633 | Dihydrorhodamine 6G |
| | | | | D-638 | Dihydrotetramethylrosamine |
| | | | | M-7511 | MitoTracker Orange CM-H2TMRos* |
| Probes for Acidic Organelles, Including Lysosomes -- see Section 12.3 | | | | | |
| D-1552 | DAMP § | L-7526 | LysoTrackerGreen DND-26 | D-113 | Dansyl cadaverine |
| H-7599 | Hydroxystilbamidine ¶ | L-7542 | LysoTracker Green $Br_2$ | L-7527 | LysoTracker Yellow DND-68 |
| L-7525 | LysoTracker Blue DND-22 ¶ | | | | |
| L-7537 | LysoTracker biotin § | | | | |
| L-7583 | LysoTracker biotin/DNP § | | | | |

TABLE 2-continued

Molecular Probes' organelle-selective probes
Probes for Acidic Organelles, Including Lysosomes (pH-Sensitive Probes) -- see Section 12.3

| | | | | | |
|---|---|---|---|---|---|
| L-7532 | LysoSensor Blue DND-192 ¶ | L-7534 | LysoSensor Green DND-153 | A-1301 | Acridine orange |
| L-7533 | LysoSensorBlue DND-167 ¶ | L-7535 | LysoSensorGreen DND-189 | L-7545 | LysoSensorYellow/Blue DND-160 ‡ |
| L-7545 | LysoSensor Yellow/ Blue DND-160 ‡ | | | | |

Probes for Endoplasmic Reticulum -- see Section 12.4

| | | | | | |
|---|---|---|---|---|---|
| | | B-7447 | BODIPY FL brefeldin A | B-7449 | BODIPY 558/568 brefeldin A |
| | | D-272 | DiOC5(3) | D-282 | $DiIC_{18}(3)$ |
| | | D-273 | DiOC6(3) | D-384 | $DiIC_{16}(3)$ |
| | | | | R-648 | Rhodamine B, hexyl ester |
| | | | | R-634 | Rhodamine 6G |
| | | | | T-668 | Tetramethylrhodamine, methyl ester |
| | | | | T-669 | Tetramethylrhodamine, ethyl ester |

Probes for Golgi Apparatus -- see Section 12.4

| | | | | | |
|---|---|---|---|---|---|
| B-7450 | Brefeldin A | B-7447 | BODIPY FL brefeldin A | B-7449 | BODIPY 5581568 brefeldin A |
| | | D-3521 | BODIPY FL $C_5$-ceramide‡ | | |
| | | D-3522 | BODTPY FL $C_5$-sphingomyelin | | |
| | | D-7546 | BODIPY FL $Br_2C_5$-ceramide‡ | | |
| | | N-1154 | NBD $C_6$-ceramide | | |
| | | N-3524 | NBD $C_6$-sphingomyelin | | |

Red Fluorescent Probes

| Cat # | Probe |
|---|---|
| Probes for Mitochondria -- see Section 12.2 | |
| M-7512 | MitoTracker Red CMXRos* |
| T-3168 | JC - 1 ‡ |
| Probes for Mitochondria (Probes Requiring Intracellular Oxidation) -- see Section 12.2 | |
| M-7513 | MitoTracker Red CM-H2XRos * |
| Probes for Acidic Organelles, Including Lysosomes (pH-Sensitive Probes) -- see Section 12.3 | |
| L-7528 | LysoTrackerRed DND-99 |
| N-3246 | Neutral red |
| Probes for Golgi Apparatus -- see Section 12.4 | |
| D-3521 | BODIPY FL C5-ceramide ‡ |
| D-7540 | BODIPY TR ceramide ‡ |
| D-7546 | BODIPY FL $Br_2C_5$-ceramide ‡ |

*Aldehyde-fixable probe.  † Chemiluminescent probe.  ‡ Dual-emission spectrum.  § Nonfluorescent probe.  ¶Blue fluorescent probe.

additional discriminating response information which is useful for detecting biological or chemical analytes of interest.

While a number of encoding dyes and methods are available, in one embodiment, external fluorescent cell membrane labels, PKH67 with an excitation wavelength of 490 nm and an emission wavelength of 502 nm, and PKH26 with an excitation wavelength of 551 nm and an emission wavelength of 567 nm, were utilized. PKH26 and PKH67 are part of a family of dyes manufactured by Zynaxis Cell Science (Malvern, Pa.), sold under the trademark Zyn-Linker® (Phanos Technologies Inc.), produced by the method of U.S. Pat. No. 5,665,328 to Hogan, et al., and available from Sigma (St.Louis, Mo.). In this embodiment, both dyes were applied to suspended fibroblast cells to encode the cells prior to placement in the sensor array. Encoded cells were placed in microwells filled with growth media. The encoded cells were then illuminated with excitation light transmitted through the fiber optic array and the resulting fluorescent emission response of cells was collected through the same fiber and passed to the detection system. FIG. 6 shows a typical fluorescence optical image of a PKH26 encoded cell population in a biosensor array of the present invention. FIG. 8 shows a typical fluorescence image of a PKH67 encoded cell population in a biosensor array. Note that only those microwells containing encoded cells yields a fluorescent signal upon excitation at the encoding dye wavelength.

In a typical encoding procedure, external or internal encoding labels are applied to suspended cell populations prior to placement in the sensor array. In one embodiment, an external label is applied to the cell by first washing the suspended cells with serum-free media and then centrifuging the cells into a loose pellet at 2000 RPM for 5 minutes. The supernatant is drawn off and the centrifuge tube is tapped to resuspend the cells. Approximately 1 mL of Diluent C, available as dye kit from Sigma, was added to the cells and the tube was inverted to mix. Immediately prior to encoding, a solution of $4 \times 10^{-6}$ M Diluent C dye was prepared. The suspended cells are added to the dye solution, mixed by pipetting the cell/dye solution, and incubated for 5 minutes. To stop the encoding reaction, 2 mL of fetal calf serum was added to the cells, incubated for 1 minute, and then diluted by adding 4 mL growth media. The cells are then centrifuged at 2000 RPM for 10 minutes to remove the cells from the staining solution. The supernatant was drawn off and the cells are transferred to a new tube. Finally, the cells are subjected to a minimum of three washings by adding 10 mL growth media, centrifuging, and resuspending the cells.

To demonstrate the encoding method with PKH26 and PKH67 dyes, encoded NIH 3T3 mouse fibroblast cells were dispersed in microwells in sensor array and the location of encoded cells within the array was determined by excitation of the cells at a wavelength of 551 nm. Upon excitation, the encoded cells form a characteristic, detectable fluorescence pattern within the sensor array where the pattern provides a locational template for cell viability measurements using BCECF and an excitation wavelength of 505 nm. The excitation and emission wavelengths of the PKH26 encoding label and the BCECF-AM dye are sufficiently separated so that there is no interference between the two dyes. FIG. 6 is a characteristic fluorescence image pattern identifying the location of PKH26 encoded cells in the biosensor array. A similar procedure was followed for encoding the mouse fibroblast cells with PKH67 where a corresponding characteristic fluorescence image pattern is shown in FIG. 8.

In addition to encoding individual cell populations with a single unique dye, each cell population within the array may be encoded with unique dye ratios which yield a characteristic fluorescent intensity ratio in a distinct wavelength range. A range of dye ratios may be employed with two or more dye combination for producing a series of encoding ratios useful for a identifying a large number of cell populations. The fluorescent intensity ratio, produced by a specific dye ratio which is used for encoding a cell population, can be distinguished by taking the mean intensity minus the background intensity at each emission wavelength and then dividing the two values to obtain the range for that particular ratio.

In one embodiment, two separate populations of NIH 3T3 mouse fibroblast cells were encoded by labeling cell membranes with either a 1:5 or a 5:1 ratio of PHK67 and PHK26 dyes. Each cell population comprised approximately 125 encoded cells. The cell populations were illuminated at 490 nm and 551 nm excitation wavelengths and emitted fluorescent intensity ratios were measured at 502 nm and 567 nm. Measurements of the average intensity ratio for each dye ratio were made over a two day period. The initial average intensity ratio for the 1:5 PKH67/PKH26 ratio was 0.0863 and the ratio for the 5:1 dye ratio was 0.7014. The final average intensity ratio for the 1:5 ratio was 0.2655 and for the 5:1 ratio it was 0.9090 indicating that the ratios are reasonably stable, even where cell splitting has occurred, and that dye ratio encoded cell populations remain distinguishable with time. Thus, dye ratios can provide a useful alternative encoding mechanism for identifying and locating cell populations which are randomly dispersed on a biosensor array of the present invention.

F. Indicator Dyes

The optical responses of individual cells and cell populations to chemical or biological stimuli are typically interrogated and detected by coupling individual cells with appropriate indicators which may be either fluorophores, chromophores, stains or a dye compounds. Any suitable indicator or combinations of indicators may be utilized provided the indicator does not compromise cell response. For example, conventional cell fluorophore probes such as fluoresceins, rhodamines, naphthalimides, phycobiliproteins, nitrobenzoxadiazole may be utilized. Alternatively, permeant or impermeant cell membrane potential indicators, ion indicators, reactive oxygen indicators and pH indicators may be employed. By way of example a number of indicators which would have particular utility for the biosensor array of the present invention are listed in Tables 3 through 8 together with their characteristic excitation and emission wavelengths. A particularly useful reference for selecting appropriate indicators is R. P. Haugland, *Handbook of Fluorescent Probes and Research Chemicals* ($6^{th}$ ed.), Molecular Probes Inc.(Eugene, Oreg., 1996).

In one embodiment, indicators may be incorporated directly into the cell by attachment to the cell membrane, by absorption into the cell cytoplasm by membrane permeant indicators, or by microinjection into the cell cytoplasm. In an alternative embodiment, ultrafine fluorescing microspheres, such as Molecular Probes FluoSpheres™, are ingested by the cells and are employed as indicators. In another environment, indicators are added to the culture media fluid contained within the microwells. In an alternative embodiment, indicators may be attached to the surface of the microwells by a conventional

TABLE 3

Molecular Probes' pH indicator families, in order of decreasing $pK_n$

| Parent Fluorophore | pH Range | Typical Measurement |
|---|---|---|
| SNAFL indicators | 7.2–8.2 | Excitation ratio 490/540 nm or emission ratio 540/630 nm |
| SNARF indicators | 7.0–8.0 | Emission ratio 580/640 nm |
| HPTS (pyranine) | 7.0–8.0 | Excitation ratio 450/405 nm |
| BCECF | 6.5–7.5 | Excitation ratio 490/440 nm |
| Fluoresceins and carboxyfluoresceins | 6.0–7.2 | Excitation ratio 490/450 nm |
| Oregon Green dyes | 4.2–5.7 | Excitation ratio 510/450 nm or excitation ratio 490/440 nm |
| Rhodols (including NERF dyes) | 4.0–6.0 | Excitation ratio 514/488 nm or excitation ratio 500/450 nm |
| LysoSensor probes | 3.5–8.0* | Excitation ratio 340/380 nm |

*Depends on $pK_3$ of selected probe; see Table 23.2 for $pK_3$ of each Lysosensor probe. †Applies to L-7545 only. Other LysoSensor probes allow single excitation and emission measurements only; see Table 23.2 for wavelengths.

Summary of the pH response of our LysoSensor probes

| Cat # | LysoSensor Probe | Abs/Em* (nm) | $pK_3$† | Useful pH Range† |
|---|---|---|---|---|
| L-7532 | LysoSensor Blue DND-192 | 374/424 | 7.5 | 6.5–8.0 |
| L-7533 | LysoSensor Blue DND-167 | 373/425 | 5.1 | 4.5–6.0 |
| L-7534 | LysoSensor Green DND-153 | 442/505 | 7.5 | 6.5–8.0 |
| L-7535 | LysoSensor Green DND-189 | 443/505 | 5.2 | 4.5–6.0 |
| L-7545 | LysoSensor Yellow/Blue DND-160 | 384/540‡ 329/440§ | 4.2 | 3.0–5.0 |

*Absorption (Abs) and fluorescence emission (Em) maxima, at pH 5; values may vary somewhat in cellular environments. †All $pK_3$ values were determined in vitro; values are likely to be different in cells. ‡at pH 3; §at pH 7.

Reactive pH indicator dyes

| pH Indicator | Preferred Reactive Form |
|---|---|
| BCECF | BCECF (B-1151, see Section 23.2)* |
| Carboxyfluorescein | 5-(and-6)-carboxyfluorescein, succinimidyl ester (C-1311, see Section 1.3) |

TABLE 3-continued

| | |
|---|---|
| Cl-NERF | Cl-NERF (C-6831, see Section 23.3)* |
| Dichlorofluorescein | 2',7'-dichlorofluorescein-5-isothiocyanate (D-6078, see Section 1.5) |
| Dimethylfluorescein | 5-(and-6)-carboxy-4',5'-dimethylfluorescein (C-366, see Section 23.2)* |
| DM-NERF | DM-NERF (D-6830, see Section 23.3)* |
| Naphthofluorescein | 5-(and-6)-carboxynaphthofluorescein, succinimidyl ester (C-653) |
| Oregon Green 488 | Oregon Green 488 carboxylic acid, succinimidyl ester (O-6147, O-6149) |
| Oregon Green 500 | Oregon Green 500 carboxylic acid, succinimidyl ester (O-6136) |
| Oregon Green 514 | Oregon Green 514 carboxylic acid, succinimidyl ester (O-6139) |
| Rhodol Green | Rhodol Green carboxylic acid, succinimidyl ester (R-6108) |
| SNAFL-1 | 5-(and-6)-carboxy SNAFL-1, succinimidyl ester (C-3061) |
| SNAFL-2 | 5-(and-6)-carboxy SNAFL-2, succinimidyl ester (C-3062) |
| SNARF-1 | 5-(and-6)-carboxy SNARF-1 (C-1270, see Section 23.2)* |

*Carboxylic acids require activation with EDAC/NHSS before reaction with amines (see Section 1.1).

TABLE 4

Molecular Probes' pH indicator dextrans, in order of decreasing $pK_a$

| Dye | Cat # | $pK_a$* | Measurement Wavelengths | Application Notes |
|---|---|---|---|---|
| SNAFL | D-3301, D-3302 | ~7.8 | Excitation ratio 490/540 nm detected at 580 nm<br>Emission ratio 540/630 nm excited at 514 nm | Acidic form has the higher quantum yield (see FIG. 23.7)<br>Fluorescence increases in acidic organelles |
| SNARF | D-3303, D-3304 | ~7.5 | Emission ratio 580/640 nm excited at 514 or 488 nm | Best conjugate for ratiometric emission measurements, with spectra similar to carboxy SNARF-1 (see FIG. 23.6) |
| HPTS | D-7179 | ~7.0 | Excitation ratio 470/380 nm detected at 530 nm | Spectra of dextran conjugate are significantly shifted (~20 nm) relative to free dye |
| BCECF | D-1878, D-1879, D-1880 | ~7.0 | Excitation ratio 490/440 nm detected at 530 nm | Best conjugate for ratiometric excitation measurements, with spectra similar to BCECF (see FIG. 23.3) |
| Fluorescein | D-1821, D-1823, D-1844, D-1899, D-3305 | ~6.4 | Excitation ratio 490/450 nm detected at 520 nm | Fluorescence is strongly quenched upon uptake into acidic organelles (see FIG. 23.2B) |
| Fluorescein and tetramethylrhodamine | D-1950, D-1951 | ~6.4 | Excitation ratio 495/555 nm detected at 580 nm | Conjugate incorporating both pH-sensitive and pH-insensitive fluorescent dyes (see FIG. 23.14) |
| Rhodol Green | D-7148, D-7150 | ~5.6 | Excitation ratio 500/450 nm detected at 530 nm | High photostability Most useful below pH 6 (see FIG. 23.15) |
| DM-NERF | D-3319, D-3320 | ~5.4 | Excitation ratio 510/450 nm detected at 540 nm | Useful at a higher pH than Cl-NERF dextrans (see FIG. 23.12) |
| Oregon Green 488 | D-7170, D-7172 | ~4.7 | Excitation ratio 490/440 nm detected at 520 nm | Good photostability Optimum pH sensitivity range between that of DM-NERF and Cl-NERF |
| Oregon Green 514 | D-7174, D-7176 | ~4.7 | Excitation ratio 510/450 nm detected at 530 nm | Excellent photostability Optimum pH sensitivity range between that of DM-NERF and Cl-NERF (see FIG. 23.11) |
| Cl-NERF | D-3324, D-33325 | ~3.8 | Excitation ratio 510/450 nm detected at 540 nm | Useful at a lower pH than DM-NERF dextrans (see FIG. 23.12) |

*$pK_a$ values are those determined for the free dyes. Actual values for dextran conjugates may differ by up to +/−0.3 pH units and may vary between production lots. †Radiometric emission measurements at 520/580 nm (with excitation at 495 nm) are also possible in principle; however, the response may be complicated by fluorescence resonance energy transfer.

TABLE 5

Summary of fluorescent $Ca^{2+}$ indicator available from Molecular Probes

| $Ca^{2+}$ indicator | Salt* | AM Ester† | Dextran‡ | Mode§ | $K_d$ (nM)¶ | Notes |
|---|---|---|---|---|---|---|
| Bis-fura | B-6810 | | | Ex 340/380 | 370 | 1 |
| BTC | B-6790 | B-6791 | Ex 400/480 | | 7000 | 2 |
| Calcium Green-1 | C-3010 | C-3011, C-3012 | C-6765, C-3723, C-3714, C-6766 | Em 530 | 190 | 3, 4 |
| Calcium Green-2 | C-3730 | C-3732 | | Em 535 | 550 | 3, 5 |
| Calcium Green-SN | C-3737 | C-3739 | | Em 530 | 14,000 | 3 |
| Calcium Orange | C-3013 | C-3015 | | Em 575 | 185 | 2 |
| Calcium Orange-5N | C-6770 | C-6771 | | Em 580 | 20,000 | 2 |

TABLE 5-continued

Summary of fluorescent Ca$^{2+}$ indicator available from Molecular Probes

| Ca$^{2+}$ indicator | Salt* | AM Ester† | Dextran‡ | Mode§ | K$_d$ (nM)¶ | Notes |
|---|---|---|---|---|---|---|
| Calcium Crimson | C-3016 | C-3018 | C-6824, C-6825 | Em 615 | 185 | 2 |
| Fluo-3 | F-1240, F-3715 | F-1241, F-1242 | | Em 525 | 390 | 3, 4 |
| Fura 2 | F-1200, F-6799 | F-1201, F-1221, F-1225 | F-6764, F-3029, F-3030 | Ex 340/380 | 145 | 2 |
| Fura Red | F-3019 | F-3020, F-3021 | | Ex 420/480 | 140 | 2, 6, 7 |
| Indo-1 | I-1202 | I-1203, I-1223, I-1226 | I-3032, I-3033 | Em 405/485 | 230 | 2 |
| Mag-fura-2 | M-1290 | M-1291, M-1292 | | Ex 340/380 | 25,000 | 2 |
| Mag-fura-5 | M-3103 | M-3105 | | Ex 3340/380 | 28,000 | 2 |
| Mag-indo-1 | M-1293 | M-1295 | M-6907, M-6908 | Em 405/485 | 35,000 | 2, 8 |
| Magnesium Green | M-3733 | M-3735 | | Em 530 | 6000 | 3 |
| Oregon Green 488 BAPTA-1 | O-6806 | O-6807 | O-6798, O-6797 | Em 520 | 170 | 3 |
| Oregon Green 488 BAPTA-2 | O-6808 | O-6809 | | Em 520 | 580 | 3, 9 |
| Oregon Green 488 BAPTA-5N | O-6812 | O-6813 | | Em 520 | 20,000 | 3 |
| Quin-2 | Q-1287 | Q-1288, Q-1289 | | Em 495 | 60 | 2, 10 |
| Rhod-2 | R-1243 | R-1244, R-1245 | | Em 570 | 570 | 2 |
| Texas Red-Calcium Green | | | C-6800 | Em 535/615 | 370 | 11 |

*Catalog number for cell-impermeant salt. †Catalog number for cell-permeant AM ester. ‡Catalog number for dextran conjugate. §Measurement wavelengths (in nm), where Ex = Fluorescence excitation and Em = Fluorescence emission. Indicators for which a pair of wavelengths are listed have dual-wavelength ratio-measurement capability. ¶Ca$^{2+}$ dissociation constant; measured at Molecular Probes in vitro at 22° C. in 100 mM MOPS pH 7.2, unless otherwise noted. K$_d$ values depend on temperature, ionic strength, pH and other factors, and are usually higher in vivo. Because indicator dextrans are intrinsically polydisperse and have variable degrees of substitution, lot-specific K$_d$ values are printed on the vial in most cases.
1. Similar Ca$^{2+}$ dependent fluorescence response to fura-2 but 75% greater molar absorptivity; 2. AM ester form is fluorescent (a major potential source of error in Ca$^{2+}$ measurements); 3. AM ester form is nonfluorescent; 4. Calcium Green-1 is more fluorescent than fluo-3 in both Ca$^{2+}$-bound and Ca$^{2+}$ free forms. Magnitude of Ca$^{2+}$-dependent fluorescence increase is greater for fluo-3; 5. Larger Ca$^{2+}$ dependent fluorescence increase than Calcium Green-1; 6. Can also be used in combination with fluo-3 for dual-wavelength ratio measurements, Ex = 488 nm, Em = 530/670 nm[Cytometry 17, 135 (1994); Cell Calcium 14, 359 (1993)]; 7. Mag-Fura Red has similar spectral properties, with K$_c$ for Ca$^{2+}$ = 17 μM; 8. K$_d$ determined in 100 mM Kcl, 40 mM HEPES, pH 7.0 at 22° C. [Biochem Biophys Res Comm 177, 184 (1991)]; 9. Larger Ca$^{2+}$ dependent fluorescence increase than Oregon Green 488 BAPTA-1; 10. K$_d$ determined in 230 mM KCl, 20 mM NaCl, pH 7.05 at 37° C. [Meth Enzymol 172, 230 (1989)]; 11. This indicator consists of Ca$^{2+}$ sensitive Calcium Green-1 and Ca$^{2+}$ insensitive Texas Red dyes linked to the same dextran.

TABLE 6

O$_2$ Indicators 1,3-diphenylisobenzofuran - singlet oxygen in membranes and in cells
                    Ab - 409    Em - 476
rubrene
9,10 - diphenylanthracene
                    Ab - 391    Em - 405
trans-1-(2'-methoxyvinyl)pyrene - picomole detection
                    Ab - 352    Em - 401

Nitrite Indicators 2,3-diaminonaphthalene          10 nM - 10 μM detection
                    Ab - 340    Em - 377

NO Indicators luminol                    Ab - 355    Em - 411
dihydrorhodamine - NO reacts with superoxide or hydrogen peroxide to produce peroxynitrite anions which oxidizes the dye
                    Ab - 289    Em - none Ca$^{2+}$ Indicators Bis-fura                    340/380
Calcium Green          Em - 530 - visible light excitation
Fura 2                      340/380        UV excitable    } ratiometric Ca$^{2+}$ indicator

TABLE 6-continued

| | | |
|---|---|---|
| Indo I | 405/485 | UV excitable |
| Fluo-3 | Em - 525 | } visible light excitation |
| Rhod-2 | Em - 570 | |

TABLE 7

$Mg^{2+}$ Indicators

| | | |
|---|---|---|
| Mag-Fura-2 | 340/380 | ] UV excitable |
| Mag-Fura-5 | 340/380 | |
| Mag-Indo-1 | 405/485 | |
| Magnesium Green | 475/Em 530 | |
| Magnesium Orange | 545 ex | |

$Zn^{2+}$ Indicators

| | |
|---|---|
| Newport Green | 506/535 |
| TSQ | N-(6-methoxy-8-quinolyl)-p-toluenesulfonamide |
| | 334/385 |
| | - used to localize $Zn^{2+}$ pools in the CNS |

$Cu^+$ Indicators

| | |
|---|---|
| Phen Green | 492/517 |
| | -also detects $Fe^{2+}$, $Hg^{2+}$, $Pb^{2+}$, $Cd^{2+}$, $Ni^{2+}$ at submicromolar concentrations |

$Na^+$ Indicators

| | |
|---|---|
| SBFI | Ab 339/Em 565 - UV ex |
| SBFO | 354/575 |
| Sodium Green | 506/535 - visible light ex. - employs cronn ethers |

$K^+$ Indicators

| | |
|---|---|
| PBFI | Ab 336/Em 557 |

$Cl^-$ Indicators

| | | |
|---|---|---|
| SPQ | 344/443 | follow $Cl^-$ transport with ms time resolution |
| MQAE | 350/460 | high fluorescence quantum yield |

TABLE 8

| | | |
|---|---|---|
| Fc OxyBurst Green | | } detects oxidative burst |
| Fc OxyBurst Orange | 550/574 | that occurs in phagovacuoles |
| Dichlorodihydrofluorescein Diacetate | | - monitors oxidative activity |
| ($H_2$DCFDA) | | - cell permeant |
| em 504/529 ex | | |
| Dihydrorbodamine 123 - | | investigates reactive oxygen intermediates |
| em 507/529 ex | | produced by phagocytes ---? |
| Fura Red ™ - calcium indicator - measures calcium fluxes | | |
| Dihydroethidium - respiratory burst in phagocytes | | |
| em 518/605 ex | | |
| Aequorin - Bioluminescent $Ca^{2+}$ indicator | | |
| em 430/465 ex | | | silanization treatment for bonding the indicator to the glass surface. In one embodiment, natural or genetically engineered cell lines which exhibit chemiluminescence, bioluminesence, or color changes when stimulated are used alone without need for a separate indicator since they produce intrinsic optical responses. Examples of such cells include green fluorescent protein mutants. In other embodiments, cells which express enzymes are employed with a reagent which enables an optical response, such as the generation of a fluorescent product. For example when luciferase is expressed by a cell in the presence of luciferen, the cell produces a fluorescence response when biologically stimulated.

In alternative embodiments, multiple indicators may be employed within a cell array, within a cell population, or within individual cells so as to provide for simultaneous monitoring of cell responses to a variety of different chemical or biological materials. Where two or more indicators are utilized, dyes with spectral separation of narrow spectral bandwidths are particularly useful, for example Molecular Probes BODIPY™ dyes.

G. Optical Measurements

Individual cells and populations of cells within the biosensor array of the present invention may be optically interrogated and cell responses may be monitored by employing conventional optical components known to one of ordinary skill in the art. Where external optical stimulation of cells is required to elicit an optical response, conventional light sources such as arc lamps, photodiodes, or lasers may be employed for excitation light energy. Cell responses may be monitored by conventional detectors such as photomultiplier tubes, photodiodes, photoresistors or charge coupled device (CCD) cameras. Conventional optical train components, such as lenses, filters, beam splitters, dichroics, prisms and mirrors may be employed to convey light to an from such light sources and detectors either to discrete substrate sites or through optical fiber strands to microwells that contain individual cells. The principal requirement for any particular optical apparatus configuration that is employed in optical measurements is that the combination of optical components provide for optically coupling the cells in the array to detectors and light sources. While a particular apparatus configuration that was employed in experimental optical measurements is described below, other configurations may also be employed which are functionally equivalent and appropriate suited for a particular measurement requirement.

The instrumentation used for fluorescence measurements is a modified Olympus (Lake Success, N.Y.) epifluorescence microscope which was converted from a vertical to a horizontal configuration. A schematic diagram of the measurement system 100 is shown in FIG. 9. White light from a 75 W xenon lamp 110 is collimated by a condensing lens 112, passed through an excitation filter 120, reflected by a dichroic mirror 130, and focused onto the proximal end 210 of an imaging fiber 200 with a microscope objective 140. A neutral density filter 122 may be employed for adjustment of excitation light intensity. The imaging fiber 200 is precisely positioned by an x-y micropositioner 150, available from Spindler and Hoyer (Milford, Ma.), and a microscope z-translation stage 152. Excitation light is transmitted through the fiber 200 to the biosensor array 300 at the distal fiber end 212. The emitted fluorescence light from the biosensor array is returned through the fiber 200, through the dichroic mirror 130, filtered through an emission filter 160, and detected by a PXL™ Photometrics (Tuscon, Ariz.) charge coupled device (CCD) camera 170. A magnification lens 165 may be employed if necessary. Data is processed on an Apple Power Macintosh 440 (Sunnyvale, Calif.) desktop computer 180 using IPLab 3.0 image processing software, commercially available from Signal Analytics (Vienna, Va.). While a bench-top measurement system was utilized for these measurements, in one embodiment, a compact portable measurement system may be assembled from conventional optical and electronic components.

H. Biosensor Array Applications

The biosensor, biosensor array, sensing apparatus and sensing method of the present invention can be applied to a large variety of conventional assays for screening and detection purposes. The biosensor may be configured for virtually any assay and offers a distinct advantage for high throughput screening where a plurality of encoded cell populations, which have utility in particular assays or are genetically engineered cell to provide unique responses to analytes, may be employed in a single sensor array for conducting a large number of assays simultaneously on a small sample. The biosensor array thus provides both for tremendous efficiencies in screening large combinatorial libraries and allows conduction of a large number of assays on extremely small sample volumes, such as biologically important molecules synthesized on micron sized beads. The biosensor of the present invention can be applied to virtually any analyte measurements where there is a detectable cell response to the analyte due to biological stimulation.

The biosensor array and method of the present invention utilizes the unique ability of living cell populations to respond to biologically significant compounds in a characteristic and detectable manner. Since the selectivity of living cells for such compounds has considerable value and utility in drug screening and analysis of complex biological fluids, a biosensor which makes use of the unique characteristics of living cell populations offers distinct advantages in high throughput screening of combinatorial libraries where hundreds of thousands of candidate pharmaceutical compounds must be evaluated. In addition, such a biosensor and sensing method can be utilized for either off-line monitoring of bioprocesses or in situ monitoring of environmental pollutants where the enhanced sensitivity of living cells to their local environment can be exploited.

Thus, the present invention provides methods for detecting the responses of individual cells to analytes of interest. By "analyte of interest" or "target analyte" or "candidate bioactive agent" or "candidate drug" or grammatical equivalents herein is meant any molecule, e.g., protein, oligopeptide, small organic molecule, polysaccharide, polynucleotide, etc., to be tested for the ability to directly or indirectly altering a cellular phenotype, including its optical properties. Generally a plurality of assay mixtures are run in parallel with different agent concentrations to obtain a differential response to the various concentrations. Typically, one of these concentrations serves as a negative control, i.e., at zero concentration or below the level of detection.

Analytes encompass numerous chemical classes, though typically they are organic molecules, preferably small organic compounds having a molecular weight of more than 100 and less than about 2,500 daltons. Analytes comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eucaryotic proteins may be made for screening in the methods of the invention. Particularly preferred in this embodiment are libraries of bacterial, fungal, viral, and mammalian proteins, with the latter being preferred, and human proteins being especially preferred.

The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

As described above generally for proteins, nucleic acid candidate bioactive agents may be naturally occurring nucleic acids, random nucleic acids, or "biased" random nucleic acids. For example, digests of procaryotic or eucaryotic genomes may be used as is outlined above for proteins. "Nucleic acids" in this context includes both DNA and RNA, and nucleic acid analogs including PNA.ln a preferred embodiment, the candidate bioactive agents are organic chemical moieties, a wide variety of which are available in the literature.

While the examples below provide a variety of specific assays which may be useful in configuring and employing the biosensor array and method of the present invention, they are not intended to limit either the scope of applications envisioned or the broad range of sensing methods which can be employed with a plurality of cell populations with the biosensor of the present invention.

In one embodiment, the biosensor array can be employed for remotely monitoring redox states of individual cells or cell populations in bioprocesses. For example, NADH dependent fluorescence can be measured in bacteria, fungi, plant or animal cells. NAD(P)/NAD(P)H can be measured to monitor changes from aerobic to anaerobic metabolism in fermentation processes using the method disclosed by Luong, et al., in *Practical Fluorescence,* G. Guilbault ed., Marcel Dekker (New York, 1990).

Alternatively, the biosensor array may be employed for in situ monitoring of cellular processes in response to environmental contaminants by incorporating the method disclosed by Hughes, et al., *Analytica Chimica Acta* 307:393 (1995) to provide for distinguishable cell population responses within an array. In this method, micron-sized spheres, impregnated with a fluorophore and modified on the surface with a fluorogenic enzyme probe, are ingested by cells and enzymatic activity occurs at the sphere surface, producing a detectable fluorescent signal.

In yet another embodiment, the biosensor array can be employed with genetically engineered bioluminescent bacteria for in situ monitoring and optical sensing of metallic compounds. For example, cell population responses to antimonite and arsenite may be utilized by incorporating the method disclosed in Ramanathan, et al., *Anal Chem.* 69:3380(1997) into cell populations within the biosensor array. With this method, cell plasmid regulates the expression of bacterial luciferase depending on the metal concentration.

In another embodiment, the cell populations within the biosensor array can be encoded with ATP dependent luminescent proteins, for example firefly luciferase, which are injected into rat hepatocytes for pathological studies according to the method disclosed by Koop, et al., *Biochem. J.* 295:165(1993). These cells exhibit a decrease in cytoplasmic ATP when exposed to pathological insults and changes in fluorescence directly relate to the extent of metabolic poisoning in the cell.

In one embodiment, the cell populations within the biosensor array can be encoded with green fluorescent protein [see T. Gura, *Science* 276:1989(1997); Niswender, et al., *J. Microscopy* 180(2):109(1995); Cubitt, et al., *TIBS* 20:448 (1995); Miyawaki, et al., *Nature* 388:882(1997)]. Several genetically-engineered mutants of GFP are available which have distinguishable fluorescence emission wavelengths. These proteins have additional utility as fluorescing indicators of gene expression and $Ca^+$ levels within cells.

In an additional embodiment, the biosensor array can be used in measurements of cell proliferation by in situ monitoring of calcium levels and calcium oscillations in single cells using fluorescent markers, such as aequorin or fura-2, according to the method disclosed by Cobbold, et al., *Cell Biology* 1:311 (1990).

As will be appreciated by those in the art, the assays of the invention may be run in a wide variety of ways and for a wide variety of purposes. For example, the cells may be used as a detection system for a particular analyte; the cells undergo a characteristic optically detectable change in the presence of a particular analyte. Alternatively, the cells may be used to screen drug candidate libraries for the ability to alter a cellular phenotype that is optically detectable. For example, the expression of a therapeutically relevant cell surface receptor may be increased such that the receptor can now bind a fluorescent ligand; similarly a therapeutically relevant enzyme may now be activated such that a fluorescent reaction product is generated. In this way any modulation, including both increases and descreases, may be monitored. Similarly, the use of reporter genes such as green fluorescent proteins and derivatives thereof facilitates high throughput screening for relevant analyte interactions, through the use of inducible promoters, for example.

Generally, in a preferred embodiment, a candidate bioactive agent is added to the cells prior to analysis, and the cells allowed to incubate for some period of time. By "administration" or "contacting" herein is meant that the candidate agent is added to the cells in such a manner as to allow the agent to act upon the cell, whether by uptake and intracellular action, or by action at the cell surface. In some embodiments, nucleic acid encoding a proteinaceous candidate agent (i.e. a peptide) may be put into a viral construct such as a retroviral construct and added to the cell, such that expression of the peptide agent is accomplished; see PCT US97/01019, hereby expressly incorporated by reference.

Once the candidate agent has been administered to the cells, the cells can be washed if desired and are allowed to incubate under preferably physiological conditions for some period of time.

The reactions outlined herein may be accomplished in a variety of ways, as will be appreciated by those in the art. Components of the reaction may be added simultaneously, or sequentially, in any order. In addition, the reaction may include a variety of other reagents may be included in the assays. These include reagents like salts, buffers, neutral proteins, e.g. albumin, detergents, etc which may be used to facilitate optimal detection, and/or reduce non-specific or background interactions. Also reagents that otherwise improve the efficiency of the assay, such as protease inhibitors, nuclease inhibitors, anti-microbial agents, etc., may be used.

In general, at least one component of the assay is labeled. By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

Once the assay is run, the data is analyzed to determine the experimental outcome, i.e. either the presence or absence of a target analyte, the effect of a candidate agent on a cellular phenotype, etc. This is generally done using a computer.

In this way, bioactive agents are identified. Compounds with pharmacological activity are able to alter a cellular phenotype. The compounds having the desired pharmacological activity may be administered in a physiologically acceptable carrier to a host, as previously described. The agents may be administered in a variety of ways, orally, parenterally e.g., subcutaneously, intraperitoneally, intravascularly, etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A biosensor for detecting the response of individual cells to at least one analyte of interest comprising:
    a) a substrate comprising a plurality of wells; and
    b) a population of cells comprising at least a first and second subpopulation, each cell dispersed into a different well, wherein each subpopulation is encoded with at least one optically interrogatable material.

2. A biosensor for detecting the response of individual cells to at least one analyte of interest comprising:
    a) a fiber optic bundle comprising a plurality of fibers, said fiber optic bundle comprising at least a first surface comprising wells; and
    b) a plurality of cells, each of said cells distributed into a different well, wherein each cell is encoded with at least one optically interrogatable material.

3. The biosensor of claim 1 or claim 2 wherein said wells have an internal diameter ranging from about 1 um to about 200 um, a depth ranging from about 0.25 um to about 200 um, and a volume ranging from about 1 fL to about 5 nanoliters.

4. The biosensor of claim 2 wherein said fibers further comprise a fiber core having a diameter ranging from about 1 um to about 200 um.

5. The biosensor of claim 1 or 2 wherein said wells are coated with a biologically compatible material.

6. The biosensor of claim 1 or 2 wherein an indicator compound is attached to or inserted into at least one of said cells.

7. The biosensor of claim 2 wherein said plurality of cells comprises at least two cell populations.

8. An apparatus for detecting the response of individual cells to at least one analyte of interest comprising:
    a) a biosensor array comprising:
        i) a substrate comprising a plurality of wells; and
        ii) a population of cells comprising at least a first and second subpopulation, each cell dispersed into a different well, wherein each subpopulation is encoded with at least one optically interrogatable material; and
    b) a detector optically coupled to and in optical communication with said wells on said substrate, said detector capable of detecting an optical response of said cells dispersed in said wells to an analyte.

9. An apparatus for detecting the response of individual cells to at least one analyte of interest comprising:
    a) a biosensor comprising:
        i) a fiber optic bundle comprising a plurality of fibers, each fiber comprising at least a first surface comprising wells; and
        ii) a plurality of cells, each of said cells distributed into a different well, wherein each cell is encoded with at least one optically interrogatable material; and
    b) a detector.

10. An apparatus according to claim 9 further comprising an excitation light energy device coupled to an end of said fibers.

11. An apparatus according to claim 8 further comprising an image capturing device for capturing images of detected optical responses from a plurality of said cells.

12. The apparatus of claim 11 wherein said image capturing device comprises a charge coupled device or CCD camera.

13. A method for detecting the response of individual cells to at least one analyte of interest comprising:
    a) providing a biosensor array comprising:
        i) a substrate comprising a plurality of wells; and
        ii) a population of cells comprising at least a first and second subpopulation, each cell dispersed into a different well, wherein each subpopulation is encoded with at least one different optically interrogatable material;

b) contacting said biosensor array with an analyte of interest; and c) detected an optical response of said cells.

14. A method according to claim 13 wherein said analyte of interest comprises an optically detectable label.

15. A method according to claim 13 wherein said biosensor array is contacted with a plurality of analytes.

16. A method of making a biosensor array for detecting the response of individual cells to at least one analyte of interest comprising:

a) providing a substrate comprising a fiber optic array, said fiber optic array comprising:
  i) a plurality of fibers, each fiber comprising at least a first surface; and
  ii) a plurality of wells each formed on said first surface; and b) contacting said first surface of said fiber optic array with a plurality of cells such that each cell is inserted into one of said wells.

17. A method according to claim 16 wherein said plurality of cells comprises at least two cell populations.

18. A method according to claim 17 wherein each cell population is encoded with at least one optically interrogatable material selected from the group consisting of a dye, a fluorophore, a chromophore, a chemiluminescent compound and a bioluminescent compound.

19. A method according to claim 18 further comprising indexing the location of individual cells in said array by emitted light energy produced by illuminating said encoded cells with excitation light energy.

20. A method for detecting the response of individual cells to at least one analyte of interest comprising:

a) providing a biosensor comprising:
  i) a fiber optic bundle comprising a plurality of fibers, each fiber comprising at least a first surface comprising wells;
  ii) a plurality of cells, each of said cells distributed into a different well, wherein each cell is encoded with at least one optically interrogatable material;

b) contacting said biosensor with an analyte of interest; and c) detecting an optical response of said cells.

21. The biosensor of claim 1 or claim 2 wherein said cells are encoded by attaching said optically interrogatable material to said cells.

22. The biosensor of claim 1 or claim 2 wherein said cells uptake said optically interrogatable material.

23. The biosensor of claim 1 or claim 2 wherein said cells are encoded by injecting said optically interrogatable material.

24. The biosensor of claim 1 or claim 2 wherein said cells are genetically engineered to exhibit chemiluminescence.

25. The biosensor of claim 1 or claim 2 wherein said cells are genetically engineered to exhibit bioluminescence.

26. The biosensor of claim 1 or claim 2 wherein said optically interrogatable material is a dye.

27. The biosensor of claim 1 or claim 2 wherein said optically interrogatable material is a chromophore.

28. The biosensor of claim 1 or claim 2 wherein said optically interrogatable material is a fluorophore.

29. The biosensor of claim 1 or claim 2 wherein said optically interrogatable material is a chemiluminescent compound.

30. The biosensor of claim 1 or claim 2 wherein said optically interrogatable material is a bioluminescent compound.

* * * * *

UNITED STATES PATENT AND TRADEMARK OFFICE
CERTIFICATE OF CORRECTION

PATENT NO. : 6,377,721 B1  Page 1 of 1
DATED : April 23, 2002
INVENTOR(S) : Walt et al.

It is certified that error appears in the above-identified patent and that said Letters Patent is hereby corrected as shown below:

<u>Title page,</u>
Insert Item:
-- Related U.S. Application Data
[63] Continuation-in-part of application No. 09/033,462, filed March 2, 1998, now Patent No. 6,210,910. --.

Signed and Sealed this

Sixth Day of June, 2006

JON W. DUDAS
*Director of the United States Patent and Trademark Office*